(12) United States Patent
Biondi

(10) Patent No.: US 10,639,014 B2
(45) Date of Patent: May 5, 2020

(54) METHOD AND RELEVANT APPARATUS FOR THE DETERMINATION OF THE BODY CONDITION SCORE, BODY WEIGHT AND STATE OF FERTILITY

(71) Applicant: BIONDI ENGINEERING SA, Cadempino (CH)

(72) Inventor: Andrea Biondi, Cureglia (CH)

(73) Assignee: Biondi Engineering SA, Cadempino (CH)

( * ) Notice: Subject to any disclaimer, the term of this patent is extended or adjusted under 35 U.S.C. 154(b) by 3 days.

(21) Appl. No.: 15/553,616

(22) PCT Filed: Feb. 26, 2016

(86) PCT No.: PCT/IB2016/051058
§ 371 (c)(1),
(2) Date: Aug. 25, 2017

(87) PCT Pub. No.: WO2016/135684
PCT Pub. Date: Sep. 1, 2016

(65) Prior Publication Data
US 2018/0042584 A1 Feb. 15, 2018

(30) Foreign Application Priority Data
Feb. 27, 2015 (IT) .......... 102015000007139
Sep. 8, 2015 (IT) .......... 102015000049550

(51) Int. Cl.
*A61B 10/00* (2006.01)
*A61D 17/00* (2006.01)
(Continued)

(52) U.S. Cl.
CPC ........ *A61B 10/0012* (2013.01); *A01K 29/005* (2013.01); *A61B 5/01* (2013.01);
(Continued)

(58) Field of Classification Search
CPC . A61B 10/0012; A61B 5/1077; A61B 5/4872; A61B 2503/40; A61D 17/002; A01K 29/005
See application file for complete search history.

(56) References Cited

U.S. PATENT DOCUMENTS 5,474,085 A 12/1995 Hurnik et al.
5,483,441 A 1/1996 Scofield
(Continued)

FOREIGN PATENT DOCUMENTS

EP 1537531 3/2007
EP 2027770 A2 2/2009
(Continued)

OTHER PUBLICATIONS

International Search Report for PCT/IB2016/051058 dated May 23, 2016.
(Continued)

*Primary Examiner* — Thaddeus B Cox
(74) *Attorney, Agent, or Firm* — Thomas | Horstemeyer, LLP

(57) ABSTRACT

The present invention relates to a method for calculating the body condition score—BCS, the weight of an animal and its state of fertility by means of the mathematical processing of some characteristic morphological traits of the observed subject, which makes use of at least one contact or no-contact detection device of the profile 109 of the animal, at least a data processing unit and a program that implements a specific mathematical method of interpretation. By such a method, the determination of the body condition and its synthetic index or fattening index or FI, is independent of species, race, gender, age and absolute size of the examined animal. This method is also robust to possible errors of positioning of the apparatus by an operator.

21 Claims, 17 Drawing Sheets

(51) Int. Cl.
*A61B 5/107* (2006.01)
*A01K 29/00* (2006.01)
*A61B 5/00* (2006.01)
*A61B 5/01* (2006.01)

(52) U.S. Cl.
CPC .......... *A61B 5/1077* (2013.01); *A61B 5/1079* (2013.01); *A61B 5/4872* (2013.01); *A61B 5/7253* (2013.01); *A61D 17/00* (2013.01); *A61D 17/002* (2013.01); *A61B 2010/0019* (2013.01); *A61B 2503/40* (2013.01); *A61B 2562/0219* (2013.01); *A61B 2562/0223* (2013.01)

(56) References Cited

U.S. PATENT DOCUMENTS

| | | | |
|---|---|---|---|
| 5,576,949 | A | 11/1996 | Scofield et al. |
| 5,944,598 | A | 8/1999 | Tong et al. |
| 6,377,353 | B1 | 4/2002 | Ellis |
| 6,549,289 | B1 | 4/2003 | Ellis |
| 7,853,046 | B2 | 12/2010 | Sharony |
| 8,351,656 | B2 | 1/2013 | Spicola et al. |
| 2005/0011466 | A1* | 1/2005 | Doyle, II ............... A01K 29/00 119/518 |
| 2005/0257748 | A1 | 11/2005 | Kriesel et al. |
| 2008/0273760 | A1* | 11/2008 | Metcalfe ............... A01K 29/00 382/110 |
| 2009/0074253 | A1* | 3/2009 | Peacock ............... A01K 29/00 382/110 |
| 2010/0154722 | A1* | 6/2010 | Van Den Berg ..... A01K 11/008 119/720 |
| 2010/0246970 | A1* | 9/2010 | Springer ............... A01K 11/006 382/195 |
| 2011/0125062 | A1* | 5/2011 | Mulder ................. A01K 29/00 600/587 |
| 2011/0279650 | A1 | 11/2011 | Liao et al. |
| 2012/0275659 | A1* | 11/2012 | Gomas ................. G06K 9/6209 382/110 |
| 2013/0201470 | A1 | 8/2013 | Cramer et al. |
| 2013/0261470 | A1 | 10/2013 | Allison et al. |
| 2014/0029808 | A1 | 1/2014 | Lee |
| 2014/0180130 | A1* | 6/2014 | Granz ................... A01K 29/00 600/476 |
| 2015/0043788 | A1* | 2/2015 | Lee ...................... G06K 9/00362 382/110 |
| 2015/0342139 | A1* | 12/2015 | Saville ............... G01B 11/2545 119/14.08 |

FOREIGN PATENT DOCUMENTS

| | | |
|---|---|---|
| EP | 2370952 | 9/2014 |
| WO | 9604551 A1 | 2/1996 |
| WO | 2004012146 A1 | 2/2004 |
| WO | 2010063527 A1 | 6/2010 |
| WO | 2010107383 A1 | 9/2010 |

OTHER PUBLICATIONS

Krukowski, "Automatic Determination of Body Condition Score of Dairy Cows from 3D Images", Royal Institute of Technology School of Computer Science and Communication, TRITA-CSC-E 2009:009, ISRN-KTH/CSC/E--09/009--SE, ISSN-1653-5715, 2009, 89 pages.

Potential for Estimation of Body Condition Scores in Dairy Cattle from Digital Images; J. M. Bewley, et al. Department of Animal Science, Purdue University, West Lafayette, IN 47907; DG1J. Dairy Sci. 91:3439-3453 doi:10.3168/jds.2007-0836; American Dairy Science Association, 2008.

Potential of Using New Technology for Estimating Body Condition Scores Jeffrey M. Bewley and Michael M. Schutz Department of Animal Science and Food Sciences, University of Kentucky Department of Animal Sciences, Purdue University; Apr. 21 2009. 16 pages.

Curvature of Surfaces in 3-Space; Michael Garman, et al. 13 pages Verg 6; date unknown.

* cited by examiner

METHOD AND RELEVANT APPARATUS FOR THE DETERMINATION OF THE BODY CONDITION SCORE, BODY WEIGHT AND STATE OF FERTILITY

CROSS-REFERENCE TO RELATED APPLICATION

This application is the 35 U.S.C. § 371 national stage application of PCT Application No. PCT/IB2016/051058, filed Feb. 26, 2016, where the PCT claims priority to and the benefit of, IT Patent Application No. 102015000007139, filed Feb. 27, 2015, and IT Patent Application No. 102015000049550, filed Sep. 8, 2015, all of which are herein incorporated by reference in their entireties.

The present invention relates to a method for the determination of body condition score (BCS), body weight and the fertility status of a living being.

Moreover, the present invention also relates to apparatuses for the evaluation of the body condition score, body weight and state of a living being fertility, which implement the method.

More precisely, the present invention relates to a method for calculating the body condition score or BCS by the processing of the profile of one or more anatomical regions of the observed subject, which makes use of at least a profilometer, at least a data processing unit and at least a program that implements a specific processing of the profile. Said profile is defined here as the shape of the curve that describes at least part of the external perimeter of a section of an anatomical region of the subject under examination, such a curve lying on an imaginary plane intersecting said anatomical region. In particular, the method according to the present invention requires a profile whose size and shape are linked by any proportionality relation (also unknown) with the absolute size and physical shape of the subject.

Said method introduces a new dimensionless indicator of body condition, called Synthetic Fattening Index or Fattening Index FI or R index, which, unlike the Body Condition Score, turns out to be invariant with respect to species, breed, sex, age and absolute size of the observed subject.

This method also allows to determine, with good approximation, the body weight of a living being on the basis of the fattening synthetic index FI (or the equivalent body condition score) and other information characteristics of the subject, such as species, breed, sex, age.

This method also introduces a new indicator of the state of fertility of the observed subject. This index is the combination of the fattening index FI (or the equivalent body condition score) with the state of estrus. The only indication of estrus is commonly used today to maximize the chances of success in artificial insemination. However, a subject can be in estrus, but not having a body condition suitable for conception. The fertility index here introduced and implemented has the purpose of perfecting the estrus indicator enriching it with the information of the body condition, obtaining the Fertility Index F.

The method introduced here for the measurement of body condition score, weight and fertility index also turns out to be robust to possible errors in the use of the apparatuses by an operator and to possible skeletal variations between different subjects.

Said method also has the advantage over the known prior art to be able to be implemented even on simple devices (e.g. smartphones) without need for additional apparatuses. This is a direct consequence of the fact that in the method of the invention the profile is analyzed, leaving its absolute physical size aside.

State of the Art

Every living being, in order to perform its biological functions, needs energy always available. As far as the animal kingdom is concerned, to which the invention is addressed, the energy is extracted from food and stored in the organism in the form of fat reserves.

The Body Condition Score or BCS is a method of assessment of the body condition of an animal, or of its energy reserves, traditionally performed in a visual and/or tactile way by a properly trained technician.

Normally, in the case of the evaluation of body condition in cattle, this score is determined on the basis of a scale from 1 to 5 (other different scales are used in different nations, however they are inter-related by linear transformations), in which the minimum score 1 corresponds to a very skinny subject and the maximum score of 5 corresponds to an obese subject.

The intermediate scores indicate: 2 slender person, 3 in-shape person, 4 fat person.

The above scale also provides for intermediate scores of quarters of point, such as the scores of 2.25 or 3.75, and the like.

In the following, the BCS measured on a scale from 1 to 5 will be considered, although, around the world, BCS scales with scores ranging from 0 to 5 (in France), from 1 to 9 (or the like) are utilized, which are in any case mutually linked to one another by means of a linear transformation.

Being the BCS a subjective visual evaluation and depending on the breed and species, considerable differences were noted between the surveys carried out by different technicians (problems of subjectivity and repeatability of the assessment). This results in significant errors in the application of the predictive models described in the prior art, that are based on BCS for the assessment of animal wealth, for the balance of the food ration in specific phases of the animal life, for the diagnosis of metabolic diseases, for assisted fertilization, etc.

Intensive breeding of production animals (e.g. cattle, sheep and goats, swine), the BCS is a useful analysis tool for the health status and energy balance of the animals, able to provide, by means of appropriate processing, general guidelines on used food rations and on the management of reproduction.

In the framework of herds for milk production, it was shown that the assessment of the only body weight is not a good indicator of the fat mobilization process for the production of milk. For this reason, the method of evaluation of the Body Condition Score has received considerable consideration as a means to estimate the mobilization of tissues, for example in the field of dairy cattle (Domecq et al., 1997b; Flamenbaum et al., 1995).

For ease of discussion, in the following description, mainly the specific filed of intensive livestock milking cattle will be considered, without limiting the applicability of the invention to any other species in the animal kingdom. Each consideration herein is easily translatable in the context of any other species of higher animals.

In the framework of the dairy cattle, the obesity may be the result of a feeding that is not adequate in the last 3-4 months of lactation, a period in which the milk production starts to fall naturally and beef tends to accumulate in the body excess stores.

Even excessively long periods out of lactation ("dry" period) or a too rich nutrition at this stage can lead to an excessive body condition of the animal (overcondition).

It is known that a too fat bovine is most likely subject to difficult calvings and, after calving, it will certainly present a very poor dry matter intake, with an increase of incidence of metabolic problems such as fat cow syndrome, ketosis, and the like, and consequently production drops.

An excessive thinness (undercondition) instead can cause low milk production and low content of fat in milk, because of insufficient energy and protein stores.

It is known that cows are also called calves, heifers or cows on the basis of age; in particular, the calves are the beef from zero to a year of life, the heifers from one to three years of life and cows for three years on, or under three years if they have calved at least once.

The BCS can be usefully employed for the management of heifers to evaluate, in lean subjects, the possibility that they do not grow fast enough to enable the attainment of puberty at around 13-15 months of age, with inadequate size problems at first calving and consequent low production during the subsequent lactation.

On the other hand, it is shown that too fat heifers have lower productions compared to other beef with right weight at maturity.

The body condition of the cow is in continuous change during the lactation cycle and, consequently, also the ideal BCS varies depending on the stage of lactation, according to known patterns, such as, for example, the one shown in FIG. 1 attached.

Young cows are in the condition of the negative energy balance and they mobilize body reserves to face this phase, in which, for every pound of the mobilized weight, milk production increases by about seven pounds.

Cows or beef in late lactation are in positive balance and tend to regain lost body condition immediately after calving.

In general, the BCS evaluation can provide valuable information on the health of the observed animals, whether they be for production (i.e. bovines, goats, swines, and equines) or for companion (e.g. dogs and cats).

As shown in FIG. 3 herewith enclosed, the traditional method of assessment is based on the BCS visual and tactile appreciation of pre-established areas of the body, identifiable mainly at the level of the buttocks, lower back, back, hooks, pin bone and the base of the tail, possibly in conditions of relaxed subject, because muscle rigidity may compromise the accuracy of the observation.

It is well known that this type of visual and tactile assessment of the BCS has major drawbacks, such as the high subjectivity of the evaluation, which implies a poor repeatability of the numerical value, with the passage of time, for the same technician and for different technicians, the significant amount of time taken to carry out the necessary observations on the animal and the high cost associated with continuous training of the technicians.

Recently, this method of visual and tactile evaluation has been simplified by the use of the computer means, such as application programs for personal laptops, PDAs, tablets and smartphones.

These application programs guide the evaluator in the recognition of morphological traits to be associated with a given score, so as to reduce the time required to measure, transcribe, transmit and process the BCS.

There are also more recent programs, in which one tries to reduce the number of morphological characters to be observed, so as to further reduce the time required. In any case, it is the evaluator who, although guided, expresses the judgment. Therefore, there is still the problem of the subjectivity in the measurement and its poor repeatability.

There are also programs that allow to capture photos of the animal from different viewpoints and offer the graphical tools to highlight on the image, in post-processing, the main morphological traits.

However, the images do not appear always to be of good quality, since a picture exposed in a non appropriate way may be too dark or too light, erasing the shadows that provide information on the three-dimensionality of the body surface of the observed subject. It is however the technician the one who performs the work of recognition of the morphological traits, then subjectivity character of the measurement remains.

Automatic systems have then been developed for the BCS and weight assessment by means of analysis of two-dimensional images.

An example is represented by document U.S. Pat. No. 5,474,085, wherein a static type system is described, which is running a thermographic evaluation of the animals. In this case, considering the static nature of the geometric model, the amount of pixels in the thermal image associated to an animal is directly correlated with its weight.

A further example is represented by documents U.S. Pat. Nos. 5,483,441 and 5,576,949, which describe systems that analyze a plurality of two-dimensional images, such as concurrent images from above and from the side of the animal and/or images performed in successive instants on a moving animal, within a cameras and sensors system with fixed and known geometry.

These types of systems allow determining absolute measurements, such as height, width and length, from which BCS and/or weight can be derived by comparison with animal models with known characteristics.

Another example is represented by document U.S. Pat. No. 5,944,598, which describes a system that extracts the profile of the animal from an image and determines the geometric parameters of the system, by evaluating the distance between the observed subject and the measuring tool, for example by a laser rangefinder. From the profile, morphological and/or mass assessments are derived.

The principal limitation of these assessments automated systems is the general application complexity of the solution in the framework of a stable. This implies a high cost, poor robustness of the solution and poor accuracy and repeatability of the results.

Recently, automatic systems have been developed for the evaluation of the BCS and the weight by means of three-dimensional scanning.

An example is represented by the document US20140029808, which describes a system that performs a three-dimensional scan, for example by means of time of flight (TOF) laser rangefinders, which estimate the BCS analyzing a points cloud, comparing it with a set of reference patterns associated with different values of the BCS.

Another example is represented by document U.S. Pat. No. 8,351,656, which describes a system performing a three-dimensional scan, for example by means of structured light, stereoscopic cameras and laser rangefinders, which estimate the weight by analyzing the points cloud generated by the acquisition systems and comparing it with a set of reference models.

In this case, the device is realized as a portable solution and a series of mathematical solutions are applied to determine the orientation and the location of the animal with respect to the measuring tool.

A further document, U.S. Pat. No. 6,377,353, makes use of the method described above to derive morphometric assessments.

The document U.S. Pat. No. 6,549,289 describes the same three-dimensional analysis principle using structured light, observed by a stereoscopic camera system, applied by carrying out triangulation calculations.

Even in the case of this class of solutions, the main limitation consists in the high complexity of the technological solution that poorly fits to the application field of the stable and the formation of the technicians normally operating therein.

These solutions are therefore very expensive, very delicate and hence unreliable in the application on the field.

Moreover these solutions show poor accuracy and repeatability of the results.

There are even patents as EP1537531B1 (from WO 2004/012146 A1) and EP2370952B1 also characterized by the detection of the points cloud of an anatomical region by three-dimensional scanning. These patents implement different methods of examination of the principal curvatures of the observed surfaces, which however fully exploit the characteristics of the three-dimensional scanning, which allows detecting the absolute coordinates of the detected points and then absolute size.

These methods therefore require a three-dimensional scanning system and hence they are not applicable on simple devices, such as those equipped with a single two-dimensional camera (e.g. smartphone).

Furthermore, the products based on these methods have proven to be poorly accurate and repeatable at the boundaries of measurement scale of the body condition score (e.g. BCS<2 for a very lean subject t and BCS>4 for a very fat subject), exactly where the diagnosis is most useful to define the most appropriate intervention to restore an adequate body condition type.

Other similar solutions are given in:
US 2005/257748 A1, LEROY T ET AL: "Automatic determination of body condition score of dairy cows based on 2D images", EUROPEAN CONFERENCE ON PRECISION LIVESTOCK FARMING 2, 2005, UPPSALA, WAGENINGEN ACADEMIC PUBL, NL, 1 Jan. 2005, pages 251-255, XPO09127881, ISBN: 978-90-76998-68-8,
WO 2010/063527 A1 (DELAVAL HOLDING AB [SE]; LIAO BOHAO [SE]; KRUKOWSKI MARILYN [SE]) 10 Jun. 2010,
EP 2 027 770 A2 (ICEROBOTICS LTD [GB]) 25 Feb. 2009,
Marilyn Krukowski: "Automatic Determination of Body Condition Score of Dairy Cows from 3D Images", Master's Thesis in Computer Science, ISSN: 1653-5715, 26 Jan. 2009 (2009-01-26), pages 1-89, XP055051333, D6 KTH, Stockholm, Sweden, http://www.csc.kth.se Retrieved from the Internet: URL: http://www.nada.kth.se/utbildninglgrukthlexjobblrap-portilstor/2009/rapporter09/kruk0wski_marilyn_09009.pdf [retrieved on 2013-01-28];
US 2013/201470 A1 (ALLISON DAVID [US] ET AL) 3 Oct. 2013;
WO2010/107383 At (INNOVATOR SKAANE AB [SE]; FLODMARK CARL-ERIK [SE]) 23 Sep. 2010; and
WO96/04551 A1 (MEAT RESEARCH CORP [AU]; FORREST ALEXANDER [AU]; GORDON ANTHONY JOHN [) 15 Feb. 1996.

In light of the foregoing, therefore, it is object of the present invention to provide a method and an apparatus which overcome the disadvantages of the prior art.

In particular, an object of the present invention is to implement a method for calculating the FI and relevant BCS, body weight and fertility status, which is automatic and easy to implement.

Another object of the present invention is to provide apparatuses implementing the method, which are cheap, simple to manufacture, robust and compatible with the environment of use and applicable to any animal, regardless of species, race, gender, age and absolute size.

It is therefore subject-matter of the present invention a method and apparatuses as the defined by the independent claims.

Preferred embodiments are defined in the dependent claims.

DESCRIPTION OF THE INVENTION

The present invention will be now described, for illustrative but not limitative purposes, according to its preferred embodiments, with particular reference to the figures of the accompanying drawings, in which:

FIG. 1 shows a prior art graph representing the typical trend of the body condition score value (dashed line) and milk production (continuous line) of a bovine in good health as a function of days of lactation (reported in abscissa);

FIG. 2 highlights some examples of the anatomical region of morphological interest, such as the lumbar (L), abdominal (A), sacral (S), femoral (F), pectoral (P), gluteal (G) and dorsal (D) region in different species of animals and in man;

Subject-matter of the present invention are an apparatus and a method for the calculation of a new fattening synthetic index FI by detection and processing of some morphological traits in animals. From the latter the body condition score or BCS is derived. The combination of said FI and other parameters characteristic of the morphology and behavior of the observed subject, the body weight and a synthetic assessment index of fertility status are calculated.

Figure 5:
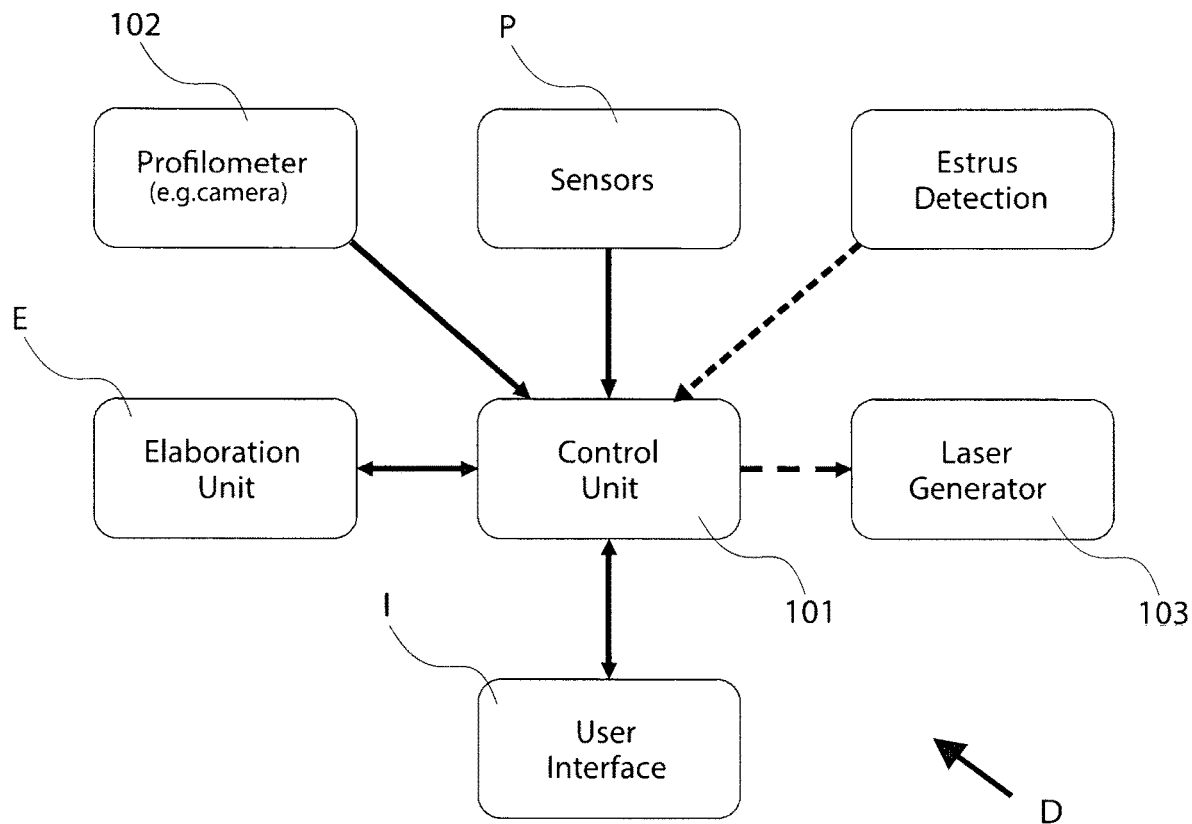
FIG. 5 shows a block diagram of the apparatus of the present invention.

Referring to FIG. 5, an apparatus D is shown for the method according to the present invention, wherein said method consists in detecting a profile of one or more anatomical regions of the observed subject, which makes use of at least a profilometer, of at least a data processing unit and at least a program that implements a specific processing method. Said profile is here defined as the shape of the curve that describes at least part of the outer perimeter of a section of an anatomical region of the subject under examination, such a curve lying on an imaginary plane intersecting said anatomical region. In particular the method according to the present invention requires a profile whose size and shape are linked by any relationship of proportionality (also unknown) with the size and the absolute physical shape of the subject.

Said profile is then processed by a data processing unit, in order to obtain an numerical synthetic index representing the fat reserves, and then the body condition of the subject itself. The apparatus D comprises at least a profilometer (which in the case of the figure is constituted by a camera 102), at least a control unit 101 and at least a data processing unit E. In the case wherein the data processing unit is remote, the apparatus D will include at least a data communication unit.

There a number of physical principles used to detect, with or without contact, said profile on a space curved surface. Among them, there are someone which are particularly suited to the field under examination. By way of example, but not of limitation, some particular applications of these principles will be illustrated, according to the purposes of the present invention. It is possible to split these applications into two main categories: (a) detection of the profile without contact, (b) detection of the profile with contact.

In general, it is worth considering that, according to the purposes of the present invention, the method used must be compatible with the application in the open field, in the case of living animals with a more or less irregular mantle, depending on the species and breed.

Among the non-contact applications between the instrument and the body of the subject under consideration, the solutions based on the analysis of images detected by two-dimensional camera are comprised.

In this case, in order to highlight a specific anatomical region of the observed subject, so that it can be detected by means of a video recording apparatus, a structured light source can be used. Assuming that the pattern consists of one or more rows transverse to the spine of the observed subject in a specific anatomical region (e.g. lumbar (L), abdominal (A), sacral (S), femoral (F), pectoral (P), gluteal (G), dorsal (D), or skull region in some special cases), it is possible to project a pattern (structured light) on the body of the subject under examination, in the anatomical region of interest. In this case, the apparatus D will include a coherent (e.g. a laser line generator) or not coherent 103 light source, this light source projecting on the subject a set of discrete or continuous points, in order to highlight a profile 109 of the morphological interest region.

This method uses the principle of optical triangulation, a technique that allows calculating the distances between points by exploiting the properties of triangles. This principle requires the exact knowledge of the relative position of the camera relative to the structured light source and the object observed, as this is essential in order to calculate the absolute coordinates in the space of detected objects.

In the method according to the present invention there is no need of knowing the absolute size of the observed subject, therefore the principle of optical triangulation can be applied regardless of the relative position of the camera with respect to the structured light source and the object observed.

Such a feature allows highlighting the anatomical region of interest even with other techniques, such as:

a) drawing a pattern on the body of the subject or animal, in the anatomical region of interest, for example by painting with a colorful paint a set of discrete or continuous points (e.g. line transversal to the spine);

b) highlighting the anatomical region of interest by applying an adhesive film, that represent the pattern to use for the subsequent step of analysis;

c) highlighting the anatomical region of interest by applying an elastic band, which represents the pattern to use for the subsequent step of analysis, around the anatomical region of interest.

In this case the principle of optical triangulation is also used, but, lacking information about the geometry of the measurement system, it is possible to solely detect information of proportionality and not to get absolute measures. For the method according to the present invention, the information of proportionality is sufficient, even if the detections containing absolute measurements can be exploited.

Figure 6A:
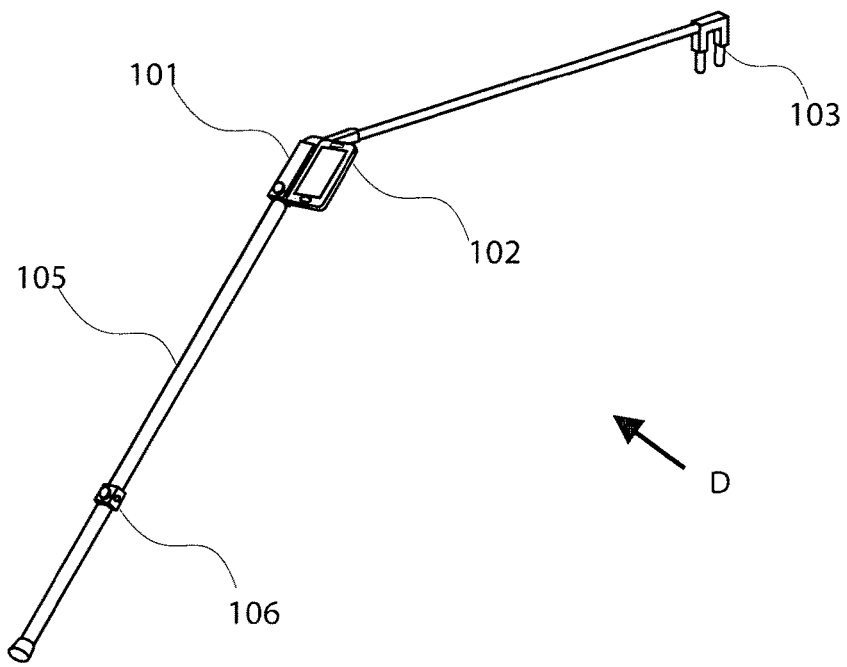
FIG. 6a shows a first embodiment of the apparatus of FIG. 5, of portable type with manual control, which implements a profilometer of the optical type.
Figure 6B:
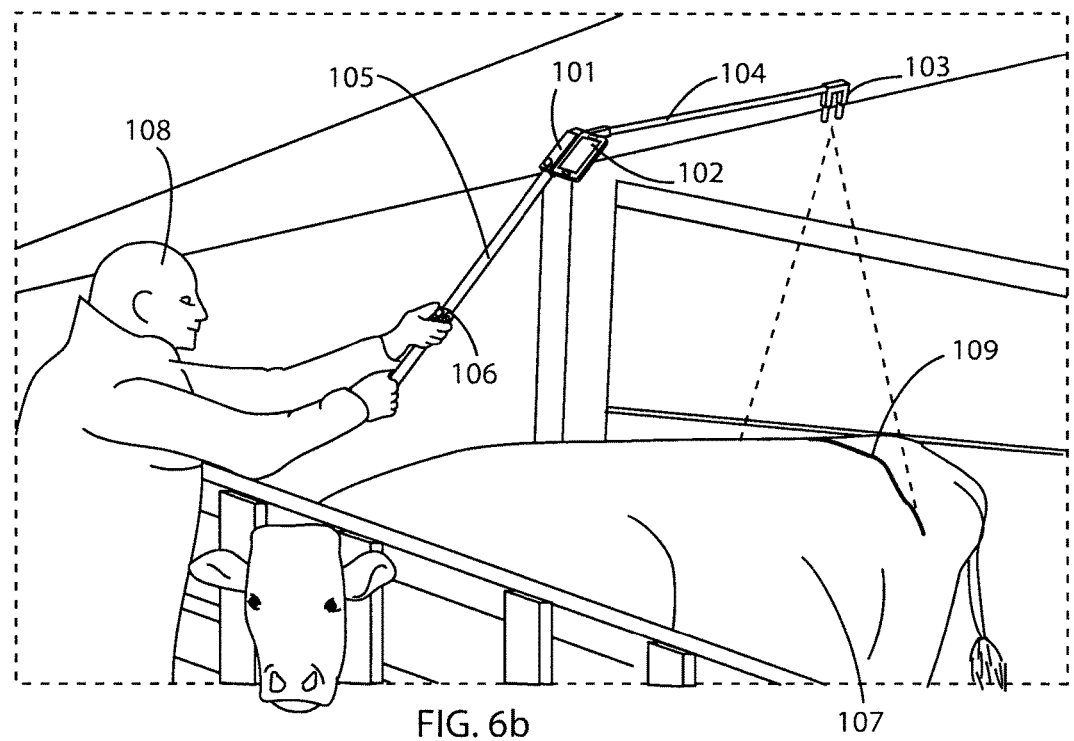
FIG. 6b shows the apparatus of FIG. 6a in use by a technician in the field of a stable of dairy cattle.
Figure 7:
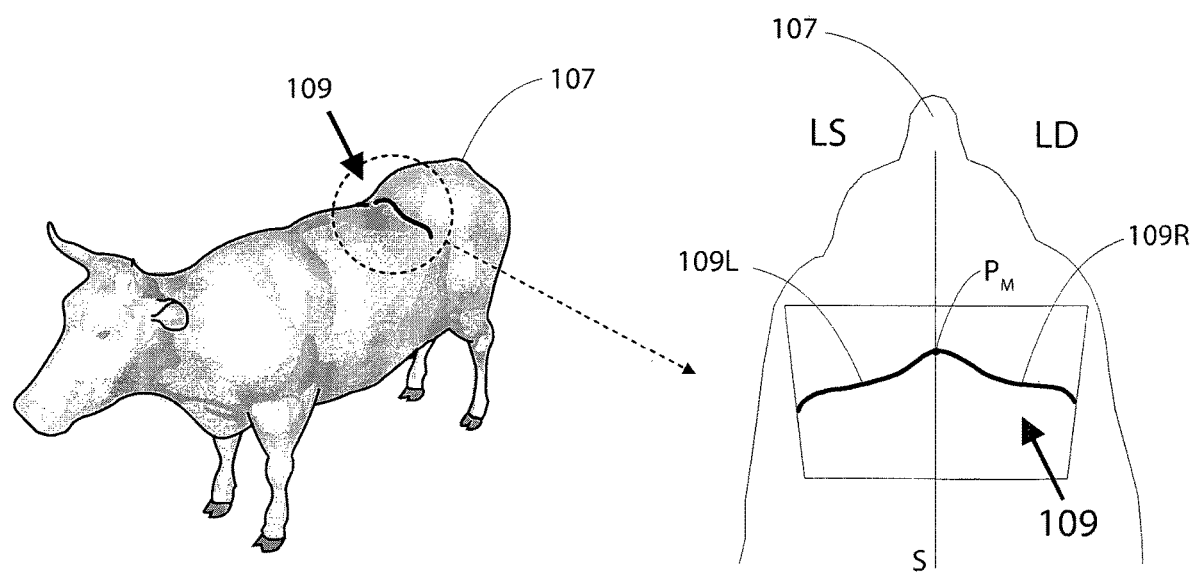
FIG. 7 shows lumbar profile in a dairy cow, in a view from above.

Preferentially, the used pattern corresponds to a line in high contrast with respect to the surface color of the observed subject, positioned transversely to the spine in the median area of the specific anatomic region under examination (for example the loins, halfway between the protuberances of the hips and the beginning of the chest, as shown in the case of cattle in FIGS. 2*a*, 6*b* and 7).

In the framework of such contour detection solutions 109 without contact, the apparatus D comprises a camera 102, adapted to acquire at least a two-dimensional image of said profile, highlighted with one of the described methods.

Alternatively, the camera can be of three-dimensional type (3D scanner), for example time-of-flight (TOF) type or of stereoscopic type, combined with a control unit that extracts the profile 109 from the cloud of the three-dimensional scanning points. In this case it is sufficient to focus on the anatomical region of interest, without highlighting the profile with one or of the described methods.

The fact is stressed that the present method is independent of the detection of absolute measurements, therefore it can be applied indifferently on conventional cameras (2D) and three-dimensional cameras (3D), e.g. stereoscopic, time of flight, or phase shift type. For this same reason the relative position of the recording device with respect to a possible laser generator is not relevant.

Among the applications with physical contact there are those based on contact profilometers, such as the needles profilometer or gauge comb. This tool allows detecting the profile of a surface along a plane intersecting said surface and is constituted by a set of parallel needles, coplanar and aligned, movable along a direction. This tool allows detecting the profile 109 in a mechanical way. The position of the individual needles is measured and digitized in order to reconstruct a computerized image of the profile 109.

Even between applications with physical contact there are those consisting in detecting the contour 109 by flexure sensors. This system consists of a sequence of sensors positioned continuously along a band. Each sensor indicates their degree of flexure to a control unit which determines the relative position of all the sensors along the strip, reconstructing a computerized image of the profile 109.

All possible implementations described herein produce as output an image of the profile 109 that the control unit 101 pre-processes and sends to the data processing unit E.

The apparatus that implements the method according to the present invention can comprise also position sensors P, including the tilt sensor such as accelerometers, gyroscopes and magnetometers.

Said apparatus may also include spatial location systems (e.g. global positioning system, or GPS).

Said apparatus can further comprise a radiofrequency reader (e.g. RFID ISO11784-785) that facilitates the electronic identification of animals.

Said apparatus may further comprise a system for the identification and real-time spatial location of the observed subjects (real-time locating system or RTLS) that allows detecting their instantaneous position and behavior.

Said apparatus may further comprise a system for the detection of the state of estrus of the observed subject. In the case of dairy cattle, pedometers are used (for the detection of the sudden increase of mobility in relation to the onset of oestrus), or video systems for detecting the mounting reflex by tail painting technique, or heat-sensing systems by chemical analysis of the milk or blood (e.g. detection of the concentration of progesterone). The combination of the status of estrus with the evaluation of the BCS allows defining a new index, here defined fertility index, as described below.

Said apparatus can interface with a local unit control 101, which provides for the pre-processing of the data, such as encryption and compression of data, storing within image, for example by means of watermarking techniques, accessible by means of a user interface, possibly provided with an extension arm 105 in order to simplify the proper shot of the region of anatomical interest.

These data are then transmitted to a data processing unit E that provides for their processing by an algorithm which will be described in detail in the following. The data processing unit is preferably considered remote. This solution provides more computing power, a smoother evolutionary and corrective maintenance of the code and compliance with the policy of business continuity and disaster recovery (BC/DR) for data protection.

Although, however, it does not exclude the possibility that the processing unit E can be integrated within the control unit 101.

Said apparatus D may be constituted by at least one smartphone equipped with an appropriate software application to perform the detection, a first data processing, the direct processing or the data transmission and reception and display of results.

In general, the method provides the processing in at least a data processing unit E of at least a profile as defined above by a method of processing, so as to obtain a numerical index R indicative of the amount of energy reserves in the form of fat accumulated by the animal, in particular in said anatomic region.

The method also provides correlating by means of said at least one data processing unit, by means of a predefined mathematical transform, said numeric index R with one or more state features of said animal. The numerical parameters of said mathematical transform may depend at least by species and breed of the animal and are obtained by comparison with a reference population evaluated visually according to a traditional method or a different reference method.

By making reference to the FIGS. 6a and 6b, a first embodiment of the apparatus D comprises an extension arm 105 that is gripped by a technician 108 at a first end and that supports the control unit 101 on a second end. The button 106 allows the technician to control the shutter of a photograph even when the apparatus is fully stretched in the measurement position, as illustrated in FIG. 6b.

Said control unit 101 may be in this case a smartphone, wherein the camera 102 is integrated.

At the second end of the extension arm 105 a laser arm can be optionally connected, thereby forming between them a suitable angle that render easier the positioning, by the technician 108, of the laser 103 in the lumbar region 109 of the observed animal. In a preferred, but not limiting way, this angle is of 135°. This solution is particularly advantageous in the field of dairy cattle, characterized by a significant size compared to the operator 108.

At the end of the laser arm, the laser generator 103 is connected, which is controlled by the control system 101, which receives in turn the release command from the technician 108 by means of the button 106 placed in correspondence of the first end of said extension arm 105.

Even the user interface integrated in the control unit 101 provides redundant commands and feedback control with respect to the button 106. Typically, the button 106 is useful in the event that the BCS is to be measured for subjects that are large compared to the size of the technician 108, as in the case of a bovine animal 107.

In the case of small subjects, as in the case of sheep and goats, the technician 108 can grip the arm 105 in the vicinity of the control unit 101, thus being able to interact directly with the user interface.

After that the technical 108 will have shown the body region under observation by one of the methods outlined above (wherever necessary), he will position the apparatus D in order to shoot with the camera 102 that region.

The technician 108 presses the actuator 106 to adjust the profile 109 by the camera 102.

The purpose of such apparatus D is to detect at least a profile 109 of at least a region of morphological anatomical interest (e.g. lumbar (L), abdominal (A), sacral (S), the femoral (F), start number (P), gluteal (G), dorsal (D)) of the subject 107. Other regions may also be of interest, although for special cases (e.g. wild animals).

Said profile is here defined as the shape of the curve that describes at least part of the outer perimeter of a section of an anatomical region of the subject under examination, such a curve lying on an imaginary plane intersecting said anatomical region. In particular, the method according to the present invention requires a profile whose size and shape are linked by any relationship of proportionality (also not known) with the size and the absolute physical form of the subject.

The control unit 101, by using known techniques, encrypts and compresses into a single packet the image, the personal data of the observed subject and, if available, the data recorded from the following sensors:

a) sensors of position P, such a san accelerometer and/or a magnetometer and/or un gyroscope and/or a GPS and/or a Wi-Fi localizer;

b) RFID identification systems and the like;

c) real time identification and location systems RTLS and the like;

d) systems for estrus detection or heat detection and the like.

The control unit 101 provides then the transmission of said encrypted and compressed data packet to the data processing unit E.

Such data processing unit E provides for the decryption, using known techniques, of the received information, recording them in a database and associating them to the records of the subject under consideration 107.

The data processing unit E shall then extract and process the image, automatically or semi-automatically, with appropriate prior art procedures for digital processing, in order to extract in an efficient and effective way the coordinates of the pixels which describe the profile 109 in the domain of the image.

The coordinates of these pixels can then be used to determine, according to the method which will be hereinafter described, the points of maximum $P_M$, tangency $P_1$ and $P'_1$ and intermediate points $P_2$ e $P'_2$, shown in FIGS. 7 and 8.

By mathematical formula that will be indicated below, the processing unit E can calculate the value of a fattening synthetic index FI, from which the BCS is to be derived, associate it to the measurement date and store it into a database in the record of the subject under examination 107, properly identified by a unique identification number.

Figure 9:
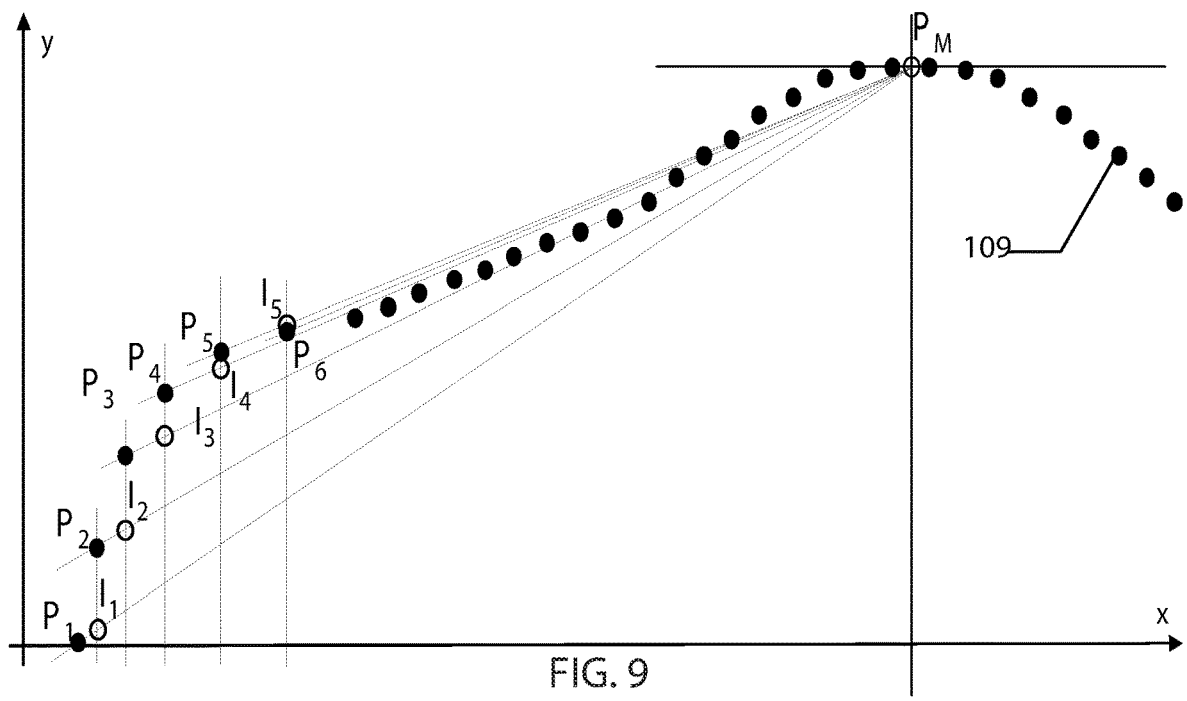
FIG. 9 shows the step of determining the points of tangency to the profile according to the method of the present invention.
Figure 10:
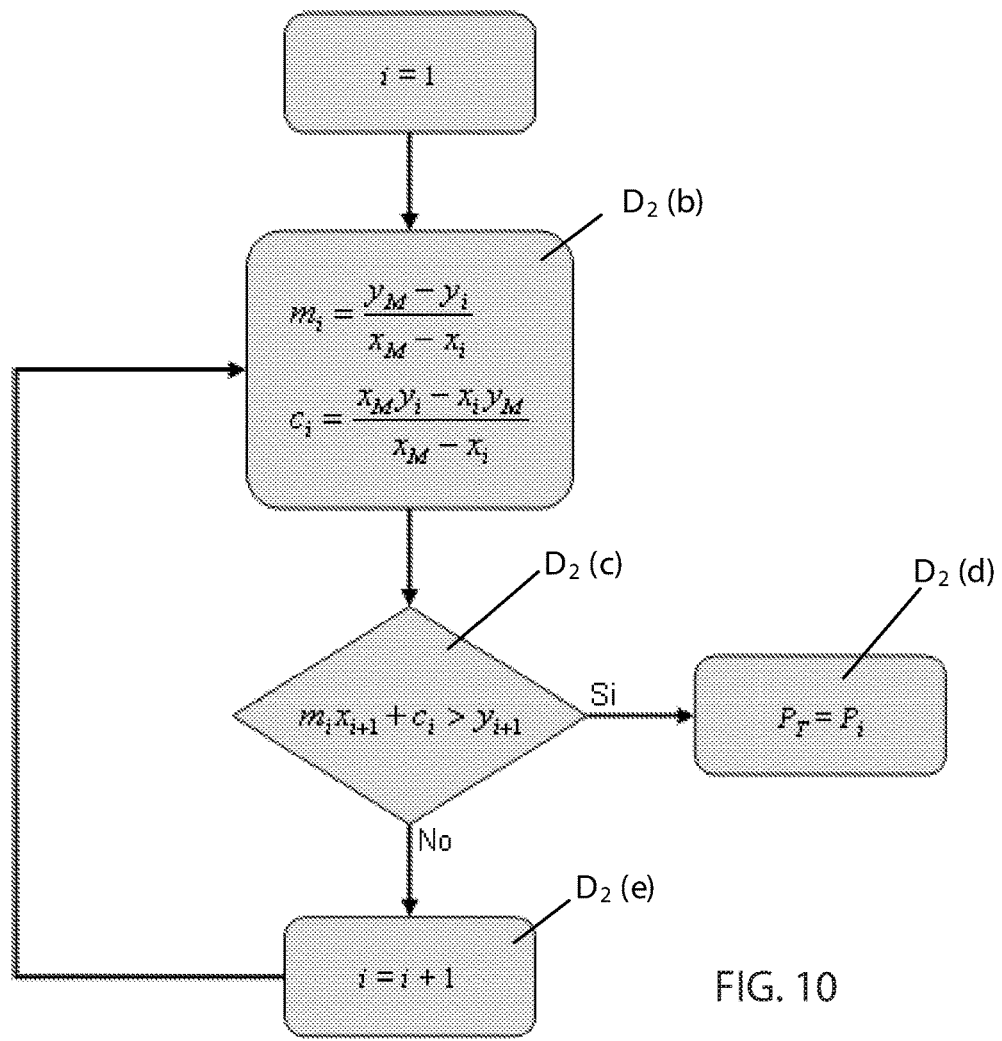
FIG. 10 shows a block diagram of the method of determination of the points of tangency to the profile.

Referring to FIGS. 9 and 10, the method of determining the FI subject of the invention, turns out to be applicable regardless of species, race, gender, age and absolute size of the observed subject 107.

The method is also robust to possible errors of use of the apparatuses by an operator and/or to the skeletal variations between different subjects.

The method of evaluation of the fattening synthetic index, corresponding to the body condition of the observed subject, is based on the assessment of fat present in at least one region of anatomical morphologic interest (e.g. lumbar (L), abdominal (A), sacral (S), femoral (F), pectoral (P), gluteal (G), dorsal (D)) of the subject 107.

Figure 18:
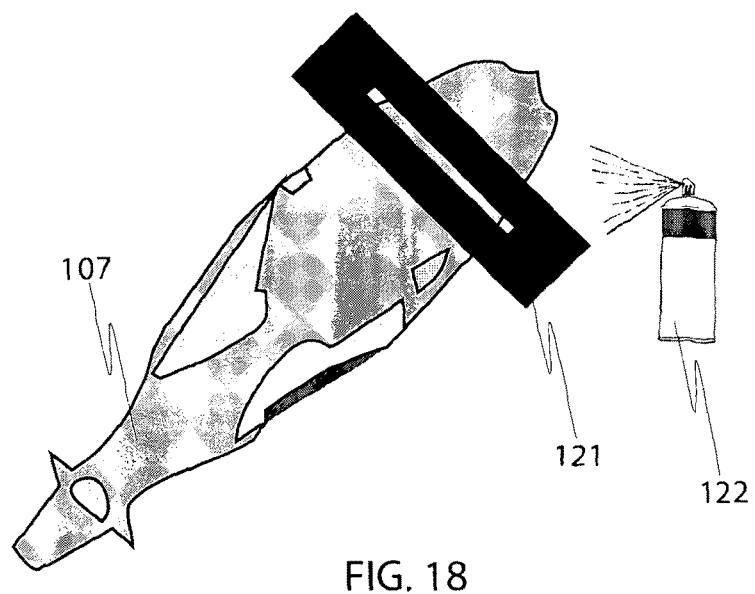
FIG. 18 shows a first example of highlighting of the profile by means of colored paint applied manually.
Figure 19:
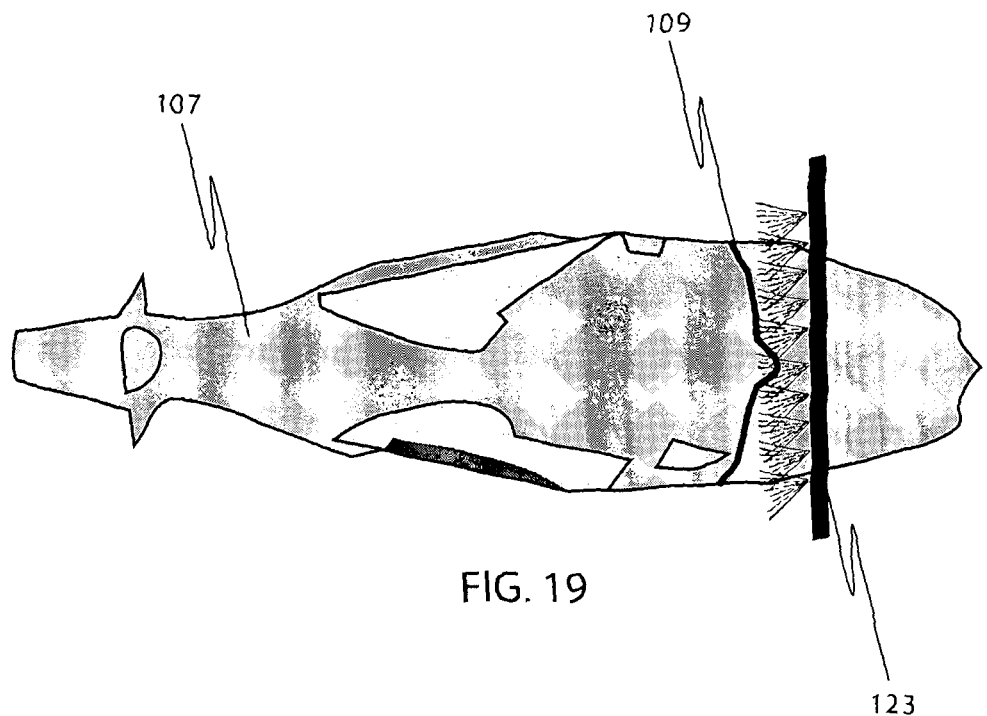
FIG. 19 shows a second example of highlighting of the profile by means of colored paint applied automatically.

A method of calculation is proposed, which takes into consideration a profile 109 of an anatomical region of the subject 107. Said profile can be obtained with an optical triangulation profilometer using a two-dimensional camera in combination with one of the following methods of highlighting the anatomical region of the observed subject. The first method is to use a colored paint to draw a suitable pattern in the selected anatomical region. Such a paint can be, for example, manually applied with a brush or a crayon, in order to obtain a line transverse to the backbone. Similarly, a pre-cut adhesive template can be used, that is applicable to said anatomical region, above which the colored paint is to be sprayed by a spray tool (see FIG. 18). A further possibility is to automate the application by means of a tool provided with a suitable number of nozzles so as to spray the paint according to the defined pattern in a manual or automatic way (see FIG. 19). Characteristics of that painting or chemical treatment must be the high degree of permanence, water resistance, solar radiation and abrasion resistance. Additional characteristic of such a treatment should be the easy detection by the camera 102 of the device in all light conditions. For this purpose, the varnish may be for example fluorescent or the chemical treatment may produce localized fall of hair (e.g. liquid nitrogen treatment).

Figure 20:
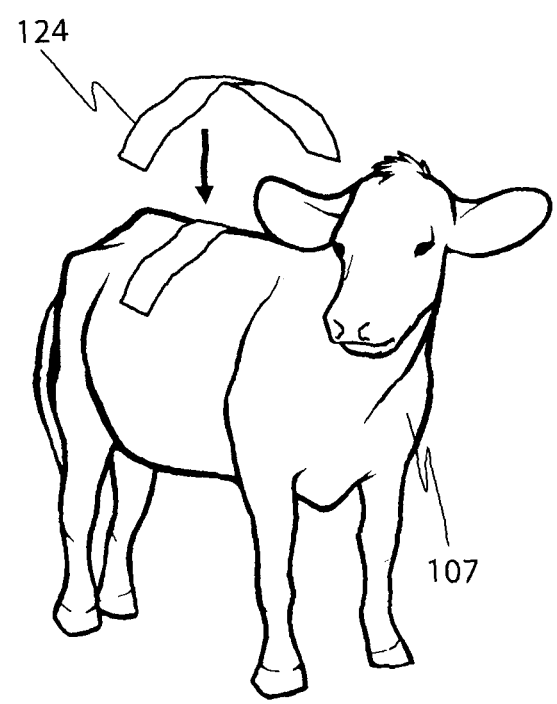
FIG. 20 shows a third example of highlighting of the profile by application of a colored adhesive.

The second method consists in applying a suitable adhesive having high contrast with respect to the surface color of the observed subject in the anatomical region of the measurement. The adhesive must show the pattern needed to carry out the measurement. For example, the adhesive can be rectangular and can be applied in said anatomical region transversely to the spine, as shown in FIG. 20. Same effect can be obtained by a suitable elastic band which reproduces the pattern in the anatomical region of interest.

The third method is to use a laser generator 103 in a position to project the reference pattern in the anatomical region of the measurement. For example, the laser may project a line transversely to the vertebral column in said anatomical region.

A second embodiment consists in the implementation of a needles profilometer or gauge comb of the electronic type. Such a device is characterized by the presence of a suitable number of needles that are parallel with each other and movable in a direction. Such needles are connected to electronic transducers producing an electrical signal proportional to the position of each needle. Such transducers are then connected to a control unit 101, which is able to extract the profile 109 of the specific anatomical region observed, as a function of the electrical signal produced by each transducer. In this case, the technician will physically rest this profilometer on said anatomical region, transversely to the spine. The profile 109 thus obtained is then transmitted from the control unit 101 and processed by the processing unit E with the method described below to determine the degree of fattening index, the body condition score, weight, etc. In this case, the mathematical transform that is used for this determination depends on at least the species and/or breed, and/or sex and/or age of the animal and is obtained by comparison with a reference population weighted by means of appropriate scales.

A third embodiment is the implementation of a flexor-electric profilometer applicable to the body of the observed subject. Such profilometer consists of an adhesive strip or an elastic band that integrates within itself suitable transducers required for the detection of the profile of said anatomical region. Such transducers may be, for example, resistive or piezoelectric. The instantly collected data allow deriving the profile 109. Such data, continuously recorded from said sensor, describe the evolution of the profile of said anatomical region along time. The technician can apply such profilometer tape as a permanent or temporary adhesive on the body of the observed subject. Similarly, such a tape may be applied by felt. Furthermore, this device could be applied under the skin. Said device may be equipped with a RTLS (Real Time Locating System). In this way, the central processing process can know at any time the identity, position and body condition of each monitored subject. Knowledge of the instantaneous position allows drawing conclusions on the behavior of the subjects. In particular on the state of estrus, as a function of certain indicators such as increasing of the movement and the reflex of immobility. As described below, the combination of the FI, or BCS, with the state of estrus, allows determining the fertility index of the test subjects. Said device can also integrate a proximity sensor or pressure so as to detect the status of estrus by the so-called mounting reflex. Indeed, at the moment when, for example, a cow is in oestrus state, it induces in her companions the covering reflex, which corresponds to the simulation by a female of a male attitude during breeding. This causes the crushing of the caudal region of the subject in estrus, which can be detected by suitable sensors. This information is added to that detectable using RTLS, to increase the accuracy.

Said device, monitoring in an almost continuous way the subject under examination, can detect other remarkable states, such as the contractions associated with calving. In the zootechnical field, in particular, the detection of the time of the delivery of a newborn turns out to be of particular importance. While the variations of the BCS are relatively slow, the calving contractions produce sudden changes of the profile 109, according to a recognizable pattern.

The profile 109 is then combined with the information from the sensors that may be present, transmitted by a control unit 101, processed by a processing unit E and processed according to the method described below to determine the fattening synthetic index, the body condition score, weight, etc.

Figure 8:
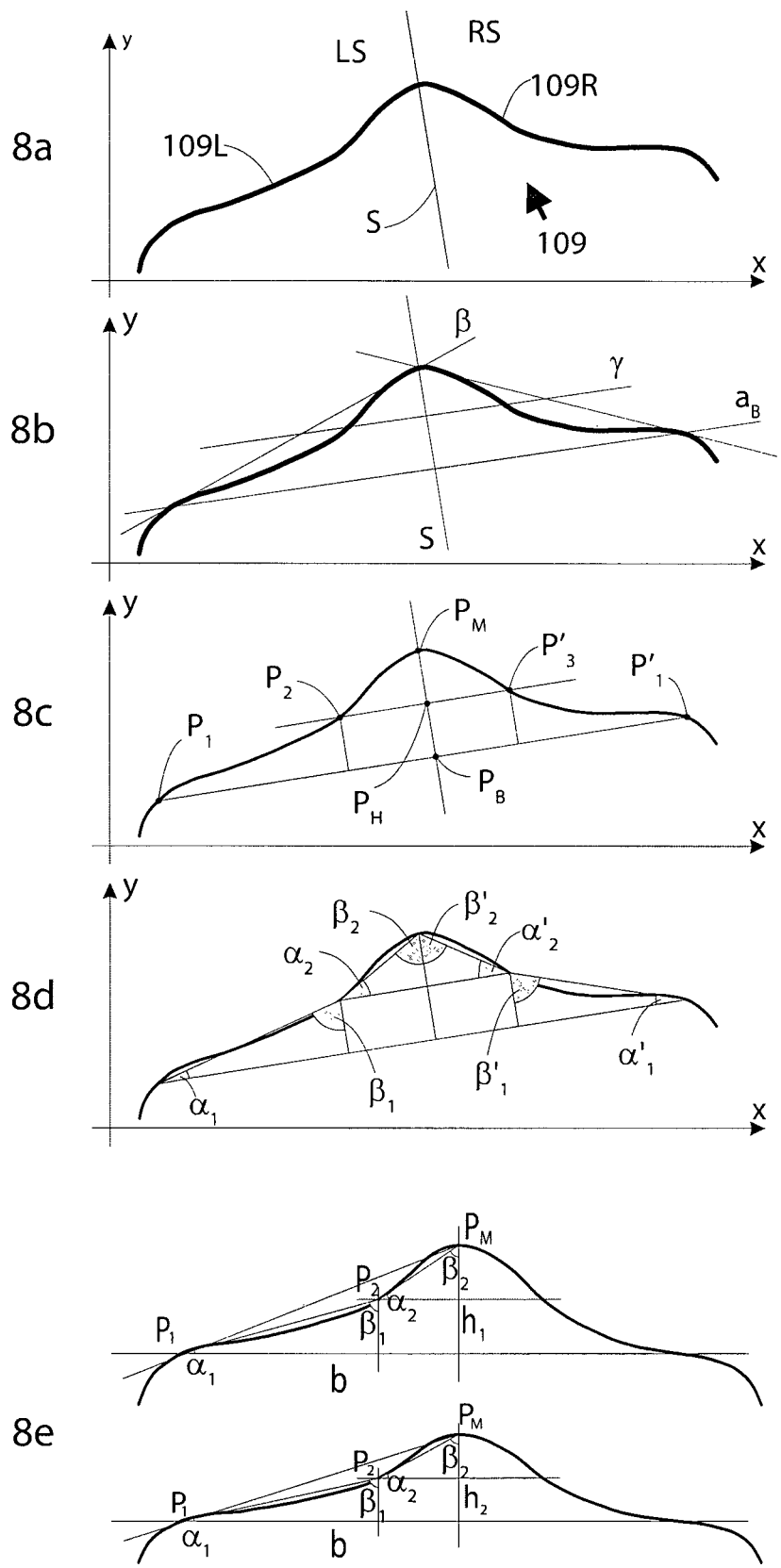
FIG. 8 shows a processing of said profile of FIG. 7.

In FIGS. 7, 8 and 9 the profile 109 is shown as produced by one of the described methods. In these representations, the case in which the subject observed is a bovine animal is considered, but the profile 109 appears to be similar in the case of other breed as well.

Figure 2:
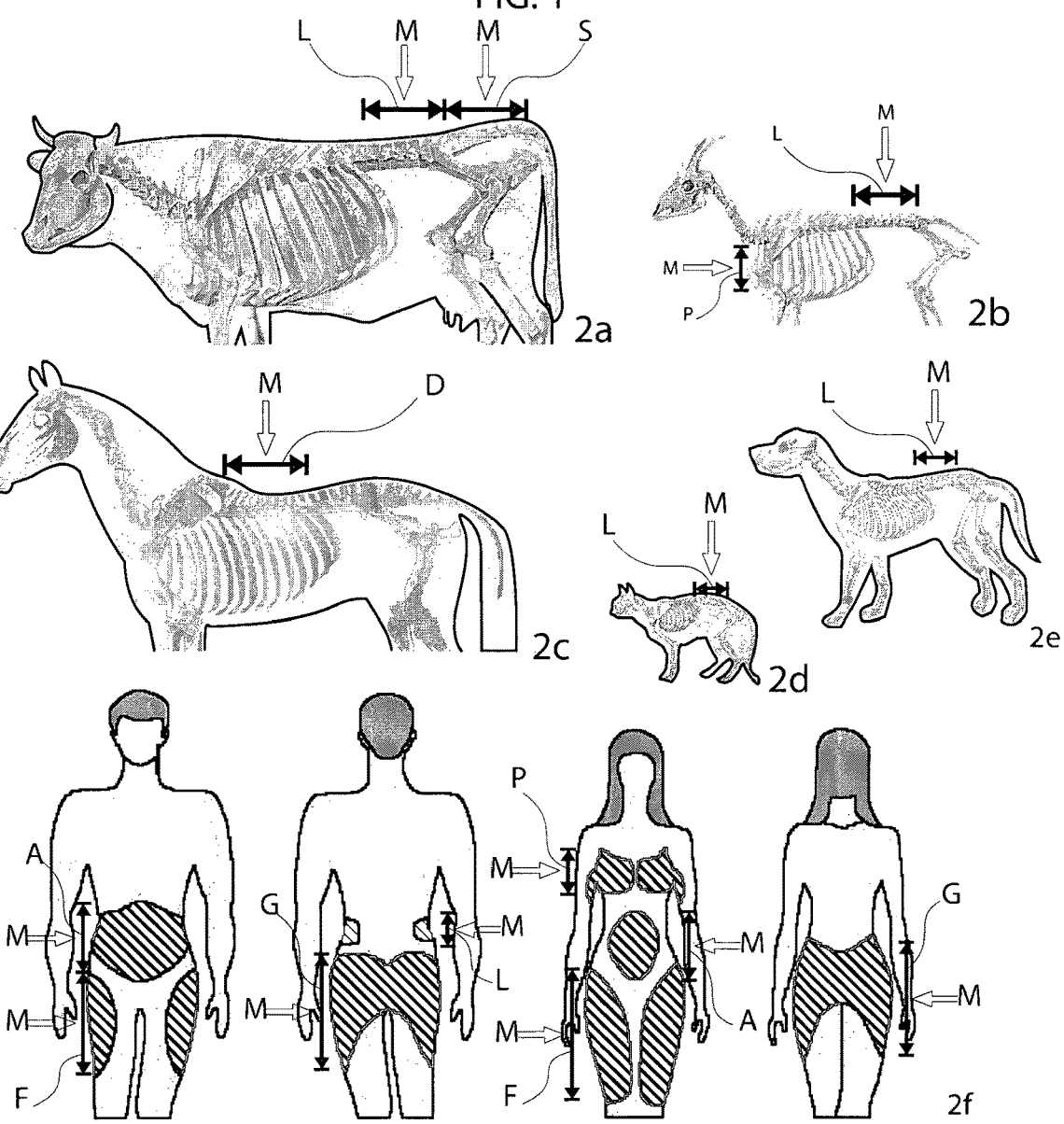

Referring to FIG. 2, in FIG. 2a the lumbar region L and sacral S in the case of cattle, in FIG. 2b lumbar regions L and pectoral P in the case of goats, in FIG. 2c the dorsal region D in the case equine, in FIGS. 2d and 2e the lumbar region L in the case of felines and canines, FIG. 2f the abdominal regions A, femoral F, gluteal G, lumbar L, femoral F and pectoral P in the case of humans are indicated.

In the median part M of said anatomical regions, a curve is produced that describes a profile according to one of the methods described.

A first side of observed subject 107, conventionally called the right side RS, and a second side opposite the first, conventionally called the left side LS are also defined.

In FIGS. 7 and 8, by way of example, a typical profile 109 of the lumbar region of a bovine is illustrated, with a left development 109L on the left side LS with respect to the direction of the back spine S, and a right development 109R on the right side LR with respect to said spine S.

The inventor has carried out extensive research that led him to determine that from the shape of said profile 109 it is possible to obtain a synthetic fattening index FI and consequently a body condition score or BCS that represents, with good approximation, the body condition of the observed subject, as shown in a section below.

The method of analysis consists in the following steps: (1) processing the profile 109 so that it is made from a sufficient number of points, such points are distributed in a uniform and homogeneous way and is provided with a certain degree of symmetry with respect to the vertebral column; (2) extracting two synthetic numerical indices representative of the left side LS and the right side RS of that profile; (3) obtaining a numerical synthetic index, here defined Fattening Index or FI, as a function of the index relative to the right side and one relevant to the left side of the profile observed in the anatomical region (specific index); (4) where the profile 109 has been detected several times in the same anatomical region, calculating their average value; (5) where more anatomical regions have been examined, defining a global synthetic index resulting from the average of the specific indices of each anatomical region; (5) obtaining the body condition score or BCS as a function of in fattening index FI, by an appropriate mathematical correlation formula, for example of the linear type.

Following the determination of the FI and the BCS, using additional characteristic data of the observed subject, such as species, breed, age and sex, the reporting method gives a good approximation of its body weight.

Moreover, the subject method allows deriving a further synthetic index, representing the fertility state, combining the FI (or the relative BCS) with the state of estrus of the observed subject. This combination is implemented using predefined mathematical transform.

It is now described, by way of example, but not by way of limitation, a possible implementation of steps (2) and (3) aimed at obtaining a synthetic index representative of the shape of the profile 109 of a specific anatomical region of the subject under examination, characterized by being dimensionless and as independent as possible from the position of the, the operator's skill, the skeletal characteristics of the observed subject.

Looking at FIG. 8, and in particular FIGS. 8c and 8b, once termed $P_M$ the point of relative maximum, let us consider a first straight line $\alpha$ and a second straight line $\beta$ passing through $P_M$ and tangent to the curve 109.

Let $P_1$ be the point of tangency between the second straight line $\beta$ and the curve 109, $P'_1$ the point of tangency between the first straight line $\alpha$ and the curve 109, $P_B$ the point of intersection between the straight line $\alpha_B$ passing through $P_1$ and $P'_1$ and the straight line S perpendicular to it and passing through $P_M$ (corresponding to the spine of the observed subject), h the segment $\overline{P_M P_B}$, $b_1$ the segment $\overline{P_1 P_B}$, $b'_1$ the segment $\overline{P'_1 P_B}$.

Let us consider a third straight line $\gamma$, parallel to the segment $\overline{P_1 P'_1}$ intersecting the straight line S in an intermediate position between $P_M$ and $P_B$.

Let $P_2$ and $P'_2$ be the intersection points between said third straight line $\gamma$ and the curve 109, h the segment $\overline{P_M P_H}$, $b_2$ the segment $\overline{P_2 P_H}$, $b'_2$ the segment $\overline{P'_2 P_H}$.

Taking into consideration FIG. 8d, let $\alpha_2$ be the angle between $\overline{P_M P_2}$ and $\overline{P_2 P'_2}$, $\alpha_1$ the angle comprised between $\overline{P_2 P_1}$ and $\overline{P_1 P'_1}$, $\alpha'_2$ the angle between $\overline{P_M P'_2}$ and $\overline{P'_2 P_2}$, $\alpha'_1$ the angle comprised between segments $\overline{P'_2 P'_1}$ and $\overline{P'_1 P_1}$.

Let angles $\beta_1$, $\beta_2$, $\beta'_1$ and $\beta'_2$ be the complementary angles of respectively $\alpha_1$, $\alpha_2$, $\alpha'_1$ and $\alpha'_2$ (i.e. such that $\alpha_i + \beta_i = \frac{\pi}{2}$).

The mathematical relationship proposed in this patent, the corresponding to the fattening synthetic index FI, for the evaluation of body condition is a function of these angles:

$$R = f(\alpha_1, \alpha_2, \alpha'_1, \alpha'_2) \quad (1)$$

Specifying a left side LS and a right side RS with respect to the spine S, it is possible to calculate R only for the left side ($R_L$) and R for the right-side only ($R_R$), obtaining R as an average of $R_L$ and $R_R$, for example, as the arithmetic average:

$$R_L = f(\alpha_1, \alpha_2),\ R_R = f(\alpha'_1, \alpha'_2) \quad (2)$$

$$R = \frac{R_L + R_R}{2} \quad (1a)$$

Alternatively, it is possible to calculate the average of the angles on the left and right side and then derive R as a function of these average angles:

$$R = f(\overline{\alpha_1}, \overline{\alpha_2}) \quad (1b)$$

wherein $\overline{\alpha_1}$, and $\overline{\alpha_2}$ are the averages of the respective left LS and right RS angles of the profile 109 with respect to the spine S, for example calculated as arithmetic means:

$$\overline{\alpha_1} = \frac{\alpha_1 + \alpha'_1}{2},$$

$$\overline{\alpha_2} = \frac{\alpha_2 + \alpha'_2}{2}$$

The index R does not measure in any way mathematically a convexity, contrary to what was assumed in the two priority documents of the present application.

A preferred form of implementation of (1), (1a), (1 b) and (2) is a function of the ratio of said angles and average angles:

$$R = f\left(\frac{\alpha_2 + \varphi}{\alpha_1 + \varphi},\ \frac{\alpha'_2 + \varphi}{\alpha'_1 + \varphi}\right) \quad (1c)$$

$$R_L = f\left(\frac{\alpha_2 + \varphi}{\alpha_1 + \varphi}\right),\ R_R = f\left(\frac{\alpha'_2 + \varphi}{\alpha'_1 + \varphi}\right),\ R = \frac{R_L + R_R}{2} \quad (2a)$$

wherein $\varphi$ is a generic angular offset, such that $\varphi \in [-\pi, \pi]$.

A preferred form of implementation of the (1c) and (2a) is as a function of the ratio of said averages of angles, according to the following formula:

$$R = f\left(\frac{\overline{\alpha_2} + \varphi}{\overline{\alpha_1} + \varphi}\right) = f\left(\frac{\alpha_2 + \alpha'_2 + 2\varphi}{\alpha_1 + \alpha'_1 + 2\varphi}\right) \quad (1d)$$

for example implementable as:

$$R = \sum_{i=0}^{n} k_i \cdot \left(\frac{\overline{\alpha_2} + \varphi}{\overline{\alpha_1} + \varphi}\right)^i \quad (1d')$$

wherein the coefficients $k_i$ are constants, n is a natural number such that $$n \geq 1, \left(\frac{\overline{\alpha_2} + \varphi}{\overline{\alpha_1} + \varphi}\right)^i$$

is the i-th power of the ratio of the average angles, which are out of phase by $\varphi$. Special case of (1d) is for n=1:

$$R = k_0 + k_1 \frac{\overline{\alpha_2} + \varphi}{\overline{\alpha_1} + \varphi} \quad (1d')$$

Particular case of (1d') is that in which $$\varphi = \frac{\pi}{2},\ k_0 = 0,\ k_1 = 1.$$

In this case, R is a function of the ratio of angles complementary to $\alpha_1$ e $\alpha_2$ (angles $\beta_1$ and $\beta_2$ of FIG. 8*d*):

$$R = \frac{\frac{\alpha_2 + \alpha'_2}{2} + \frac{\pi}{2}}{\frac{\alpha_1 + \alpha'_1}{2} + \frac{\pi}{2}} = \frac{\beta_2 + \beta'_2}{\beta_1 + \beta'_1} \quad (1d'')$$

Similarly, the (2a) can be implemented as follows:

$$R_L = \sum_{i=0}^{n} k_i \cdot \left(\frac{\alpha_2 + \varphi}{\alpha_1 + \varphi}\right)^i,\ R_R = \sum_{i=0}^{n} k_i \cdot \left(\frac{\alpha'_2 + \varphi}{\alpha'_1 + \varphi}\right)^i \quad (2b)$$

with $$R = \frac{R_L + R_R}{2}$$

wherein the coefficients $k_i$ are in constant, $n \geq 1$ and $\varphi$ is the phase shift. Special case of (2b) is for $$n = 1\ \text{and}\ \varphi = \frac{\pi}{2}:$$

$$R_L = k_0 + k_1 \cdot \frac{\alpha_2 + \frac{\pi}{2}}{\alpha_1 + \frac{\pi}{2}},\ R_R = k_0 + k_1 \cdot \frac{\alpha'_2 + \frac{\pi}{2}}{\alpha'_1 + \frac{\pi}{2}},\ R = \frac{R_L + R_R}{2} \quad (2b')$$

A further form of implementation of (1) is based on the ratio of tangents of these angles:

$$R = f\left(\frac{\tan(\alpha_2 + \varphi)}{\tan(\alpha_1 + \varphi)},\ \frac{\tan(\alpha'_2 + \varphi)}{\tan(\alpha'_1 + \varphi)}\right) \quad (1e)$$

or, individually considering the two sides LS and RS:

$$R_L = f\left(\frac{\tan(\alpha_2 + \varphi)}{\tan(\alpha_1 + \varphi)}\right),\ R_R = f\left(\frac{\tan(\alpha'_2 + \varphi)}{\tan(\alpha'_1 + \varphi)}\right),\ R = \frac{R_L + R_R}{2} \quad (1e')$$

Additional form of implementation of (1) is based on the relationship of the average of the tangents of these angles:

$$R = f\left(\frac{\overline{t_2}}{\overline{t_1}}\right) \quad (1e'')$$

wherein these averages can be calculated for example as arithmetic averages:

$$\overline{t_1} = \frac{\tan(\alpha_1 + \varphi) + \tan(\alpha'_1 + \varphi)}{2} \; e \; \overline{t_2} = \frac{\tan(\alpha_2 + \varphi) + \tan(\alpha'_2 + \varphi)}{2}$$

These formulas represent the averages of the tangents for the right side RS and the left side LS of the profile 109, with respect to the spine S.

Preferred implementation form of the (1e) is:

$$R = \sum_{i=0}^{n} k_i \cdot \left(\frac{\overline{t_2}}{\overline{t_1}}\right)^i \quad (1e''')$$

wherein the coefficients $k_i$ are constant, n is a natural number such that $$n \geq 1, \left(\frac{\overline{t_2}}{\overline{t_1}}\right)^i$$

is the i-th power of the ratio of said average values of the tangents.

Considering for sake of simplicity, by way of example, the case of n=1, $k_0$=0, $k_1$=1, $\varphi$=0, R can be calculated from (1e''') as:

$$R = \frac{\tan(\alpha_2) + \tan(\alpha'_2)}{\tan(\alpha_1) + \tan(\alpha'_1)} \quad (1f)$$

Likewise the components can be obtained only for the right side RS and left side LS:

$$R_L = \frac{\tan(\alpha_2)}{\tan(\alpha_1)}, R_R = \frac{\tan(\alpha'_2)}{\tan(\alpha'_1)} \quad (2c)$$

from which:

$$R = \frac{R_L + R_R}{2} = \frac{\frac{\tan(\alpha_2)}{\tan(\alpha_1)} + \frac{\tan(\alpha'_2)}{\tan(\alpha'_1)}}{2} = \frac{\tan(\alpha_1)\tan(\alpha'_2) + \tan(\alpha'_1)\tan(\alpha_2)}{2\tan(\alpha_1)\tan(\alpha'_1)} \quad (2c)'$$

The index R represents a new synthetic index for the assessment of body condition, that we define here the Fattening Index or FI.

A particular case is that of muscle and skeletal symmetry of the observed subject 107 with respect to the vertebral column. In this case we have that:

$$R = R_L = R_R. \quad (1g)$$

A special case is the situation in which the profile 109 is not provided in full. This may occur for example in the case where the image shot by the camera 102 is partially covered or in case the profile of a part of the anatomic region under examination is detected. This may occur in the case of production animals, for example in a slaughterhouse after the animal was slaughtered (post mortem). In this case, at the end of the slaughter line, immediately before being placed in cold storage for the hanging-to-mature process, the animal, divided into two bricks, is classified according to a standardized procedure. In Europe, for example, the classification system SEUROP is used, according to which the cattle are ranked according to category, muscle conformation and presence of fat. The shape is indicated by the letters S, E, U, R, O, P, that refer to muscle development; S exceptional with very convex profiles and high quantitative and qualitative slaughtering yields; P low, with straight profiles and low quantitative and qualitative yields.

In this context, the method here described can be advantageously applied, in the particular case in which only half of the curve represented in FIG. 8 is considered. Such a condition is covered by the particular case (1 g) wherein the two half-curves are equal and symmetrical with respect to the line of the spine.

Substantially, in this case, it deals with acquiring only one lateral development of the profile 109 and completing this curve by calculating the development on the other side as development specular with respect to the direction of the spine. The rest of the process is identical, except that the formulas are simplified thanks to the symmetry.

It is possible to apply the method for the calculation of index R several times on the same anatomical region and/or a plurality of anatomical regions of the same animal. In this case, a total index, for example as the average of the values of R of each measurement, will be calculated for example by means of the arithmetic average:

$$R = \frac{1}{n}\sum_{i=1}^{n} R_i$$

being n the number of measurements on the same animal, and $R_i$ the value of the fattening index for the i-th measurement.

The Fattening Index, calculated by formulae (1d), (1e), (1f), (2b), (2c), represents an excellent indicator of fattening state according to what has already been discussed, irrespective of species, race, sex, age and absolute size of the observed subject.

However, the resulting numerical values are not within the same scale normally used in common practice by the technical evaluators.

Figure 3:
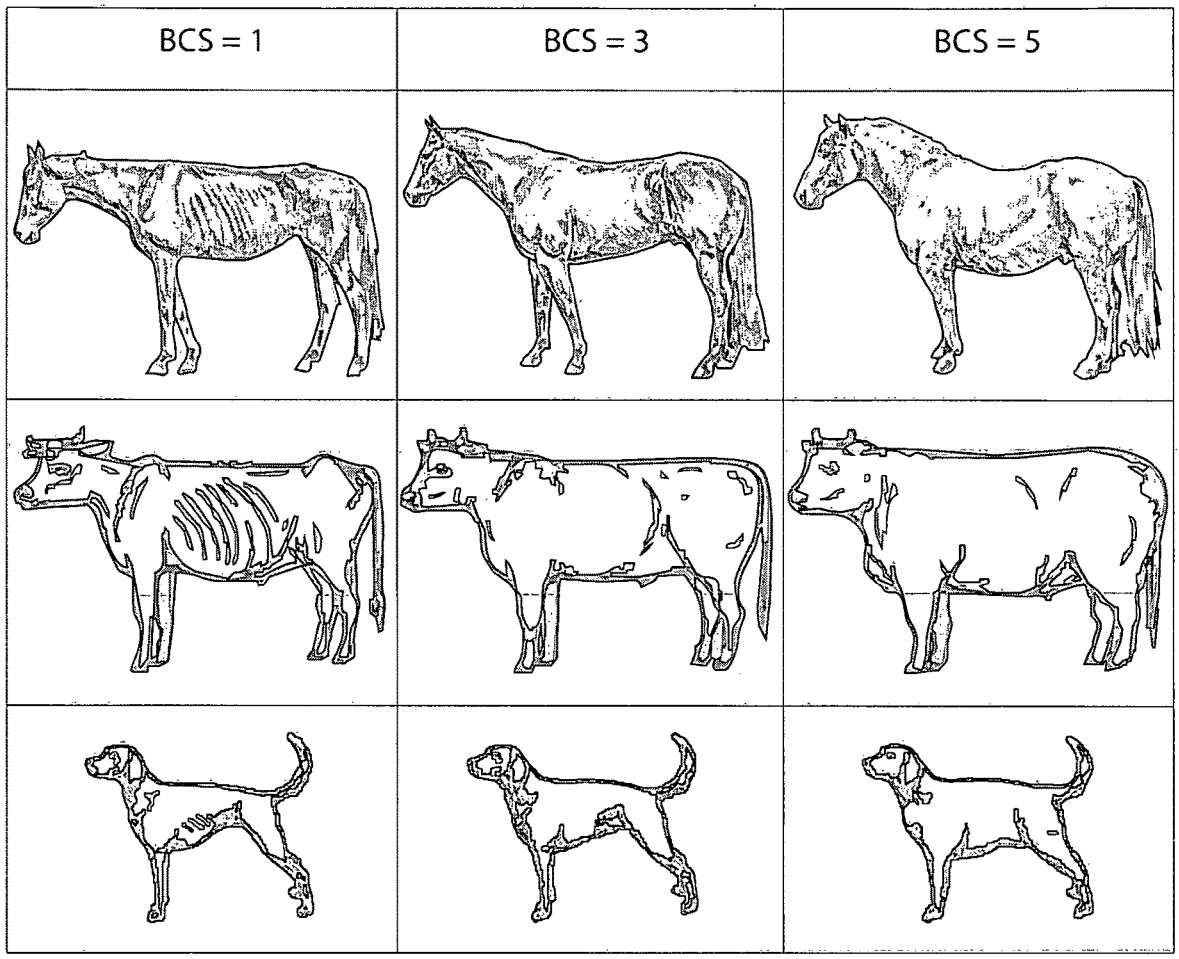
FIG. 3 shows a prior art graph relevant to the correspondence between the body condition of an animal and the relevant BCS score.
Figure 4:
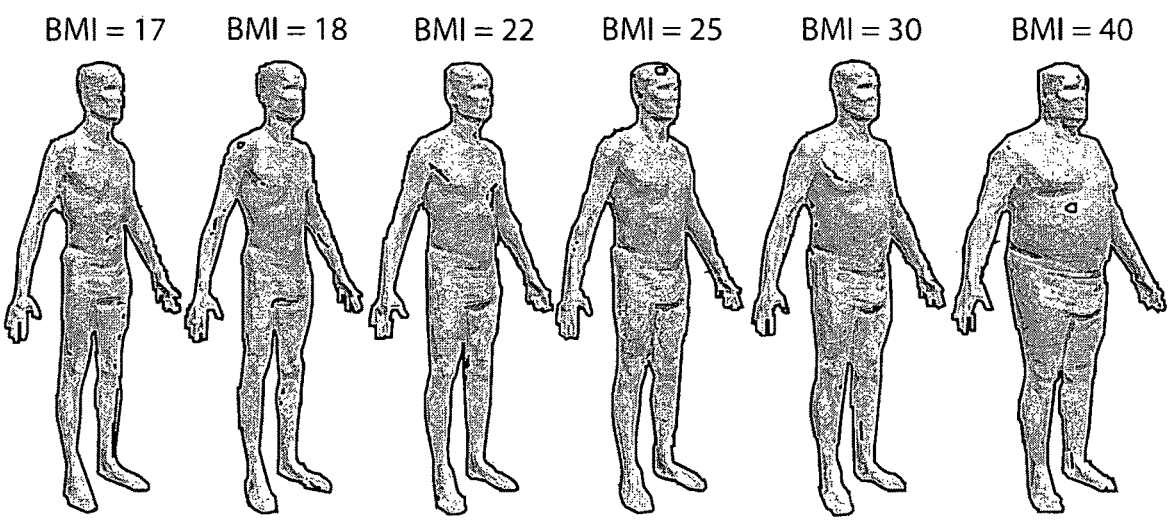
FIG. 4 shows the prior art graphs relating to the correspondence between the body condition of a human being and the corresponding BMI score.

As illustrated in FIG. 3 and according to what previously described, the index termed Body Condition Score, normally used at the international level, varies on a scale from 1 to 5 (in some countries different scales are used, such as from 0 to 5 in France or from 1 to 9, in any case related one to the other by linear transformations).

To get from R a similar score, it is necessary to apply a transform function:

$$BCS = \psi(R, S, B, M, E) \quad (6)$$

wherein R is the fattening index, S is the species, B is the race, M is sex and E is the age of the observed subject.

Setting S, B and M, and considering a specific age group, the function ψ(R,S,B,M,E) can be calculated as follows (also for other scores such as the prime body mass index):

$$BCS = \psi(R, S_0, B_0, M_0, E_0) = \sum_{i=0}^{n} k_i R^i \quad (7)$$

with $n \geq 1$ the order of function ψ. The parameters $k_i$ are coefficients depending on species, breed, sex, age group and can be determined empirically based on a group of reference subjects group whose BCS has been assessed by technical experts.

The described method is particularly effective in the determination of the BCS for Holstein breed dairy milk. The carried out tests show that the formula (7) is to be applied with a great degree of approximation with the same parameters $k_i$ to the Holstein cattle regardless of age, the stage of lactation and the number of parts (primipara or multipara heifer).

In the case of man, the most widely used synthetic index is the body mass index or BMI, defined by the following formula:

$$BMI = \frac{m}{h^2}$$

wherein m is the weight in kg of the observed subject and $h^2$ is the square of its height.

A modified version of BMI is defined as Prime BMI, corresponding to the ratio between the BMI of the observed subject and the upper limit of BMI of the reference population.

As far as the BMI Prime is a ratio of two different values of BMI, BMI Prime is a dimensionless number. Subjects with a BMI Prime of less than 0.74 are underweight; those between 0.74 and 1.00 have an optimal weight; and those higher than 1.00 are overweight. The BMI Prime is useful from a clinical point of view because it expresses in a synthetic way, for the observed subject, the percentage of deviation from the upper limit. For example, a person with BMI 34 has a BMI Prime=1.36 (with respect to an upper limit of 25), then he/she is 36% above its maximum weight.

In populations of Southeast Asia and China, BMI Prime should be used by calculating an upper limit of 23, instead of 25 (typical of Western populations).

The BMI Prime ($BMI_p$) is correlated to the index R according to a function of the type:

$$BMI_p = \xi(R, C, M, E)$$

wherein C is the group of ethnic belonging, M the sex and E the age of the observed subject.

By fixing C, M and E, one has that:

$$BMI_p = \xi(R, C_0, M_0, E_0) = \sum_{i=0}^{n} z_i R^i$$

wherein $z_i$ are coefficients determined experimentally, $R^i$ is the i-th power of index R, n is the order of the expression.

In addition to the BCS and the BMI, there are several other indexes, such as Surface-based Body Shape Index (SBSI), in any case related by a mathematical transform to the fattening index R.

An important feature of said index R is the high degree of independence from height h of the profile 109.

This implies a substantial independence of R with respect to changes in the position of the recording tool 102 or the skeletal variations between individuals of the same body condition.

For example, a variation in the relative inclination of the camera 102 with respect to the observed subject 107, the profile 109 in the real domain being equal, produces a curve, in the domain of the image, that is more or less flattened.

To illustrate this characteristic, let's take into consideration FIG. 8e. Let's consider the condition in which the technical expert detects two measurements, for example by taking two pictures, changing slightly the position of the camera between a photo and the other. This produces a change in perspective and therefore a change in the shape of the profile 109 in the domain of the image. In FIG. 8e the two curves are represented schematically as obtained as a result of the variation in the inclination of the device.

In this example, it is noted that the height h of the curve changes by 25%. It can easily be observed that the ratio of the tangents undergoes no variation and the ratio of the angles undergoes a weak variation. On the contrary, measurements such as the area of the curve undergo a very important variation.

Here are some experimental data that illustrate and confirm what was said, in reference to the curves shown in FIG. 8e.

Let's consider a profile 109 viewed from two different angles by means of a scanning triangulation system. The same condition is observable, for example, in two bovine animals with the same body condition and observed from the same instrument with the same inclination, characterized by a different skeletal structure, in particular one of the two subjects is characterized by a very prominent spine. In such possible conditions, the profile 109 in the image domain will undergo deformation shown in FIG. 8e. For example, let's consider a straight line γ such that $\overline{P_H P_B} = \frac{2}{3} \overline{P_M P_B}$.

For the first image one has:

$$\begin{cases} h_2 = 193, & b = 617, & A = 62210 \\ \alpha_1 = 16.3°, & \alpha_2 = 19.8°, & \frac{\alpha_2}{\alpha_1} = 1.22, & \frac{\tan(\alpha_2)}{\tan(\alpha_1)} = 1.23 \end{cases}$$

For the second image one has:

$$\begin{cases} h_1 = 241, & b = 617, & A = 77763 \\ \alpha_1 = 20.1, & \alpha_2 = 24.3, & \frac{\alpha_2}{\alpha_1} = 1.21, & \frac{\tan(\alpha_2)}{\tan(\alpha_1)} = 1.23 \end{cases}$$

As can be seen, a variation of 25% in the height of the curve produces a variation of 20% of the area under the curve, while the ratio of the angles it the two cases undergoes a change of less than 1% and the ratio of the tangents does not change. Since the proposed method determines the synthetic fattening index R, and consequently the BCS, as a function of the ratio of these angles, then it can be said that the FI and the BCS are sufficiently insensitive to changes in the position of the recording tool 102 with respect to its ideal location.

The fact that a deformation similar to that shown in FIG. 8e can also be due to a more or less prominent position of the spine is to be considered. Indeed, the two curves shown in FIG. 8e could correspond to two different animals, characterized by a different skeletal structure, but with the same body condition score (BCS). It is correct that the shape of the spine poorly affects the index of fatness, and consequently the BCS, because the shape of the spine does not provide any information on fat reserves accumulated by the observed subject.

This peculiarity of the proposed method shows an important difference with many of the methods of prior art that examine the absolute dimensions of the observed subject (and their processing such as the calculation of the area or volume under the curve), for example obtained by three-dimensional scanning.

By virtue of this feature and the fact that the proposed method is independent of the actual size of the flat profile 109, said method is applicable on a much wider range of devices than the methods based on the use of three-dimensional cameras (for example, time of flight, TOF, camera), such as on smartphones and in general on devices with a single camera having a low resolution.

Further optional feature of the method subject of the invention consists in the mode of determination of points $P_1$ and $P'_1$, as points of tangency to the profile 109 of the observed subject 107.

Consider, for example, to extract from the recorded image, by a digital image processing procedure, the pixels belonging to the curve 109.

Consider to have recognized N pixels, be indicated with P, the i-th pixel of the curve 109 and with $P_M$ the maximum of the curve. With reference to FIG. 9, let us consider the straight line passing through $P_M$ and P, having equation:

$$y = m_i x + c_i \quad (9)$$

wherein:

$$\begin{cases} m_i = \dfrac{y_M - y_i}{x_M - x_i} \\ c_i = \dfrac{x_M y_i - x_i y_M}{x_M - x_i} \end{cases}$$

With reference to FIG. 9 diagram, the algorithm for the determination of the point of tangency of the curve is based on the iterative comparison between the value assumed by the straight line (9) at the point of abscissa $x_{i+1}$ and the ordinate $y_{i+1}$ of point $P_{i+1}$.

The point of tangency $P_T$ is identified when the following condition is verified:

$$m_i x_{i+1} + c_i > y_{i+1}$$

The meaning of this condition is easily deduced from the FIG. 9.

The identification of the two points of tangency of the curve, indicated in FIG. 7 with $P_i$ and $P'_i$, allows to effectively apply the formula for the calculation of fattening synthetic index R and consequently the (6) for the calculation of the BCS also in the case in which the observed subject is characterized by a asymmetric conformation (e.g. cattle). In the case in which a bovine animal is observed, the internal distribution of organs determines a weak asymmetry between the right and left side. Furthermore it is frequent that the animal stands with one of the back legs more advanced with respect to the other. This implies that the profile 109R is inclined and deformed with respect to the profile 109L.

The method just described for the determination of the points of tangency $P_i$ and $P'_i$ allows overcoming this problem.

This method is also advantageous to reduce the influence on the measurement of the inclination of the measurement device with respect to the spine. The user interface can be equipped with a level indicating in real time the correct positioning of the instrument, in such a way that technician 108 is helped, at the moment of the measurement, in placing the instrument in an appropriate way.

With the algorithm of individuation of the points of tangency just described the set of effectively significant points of the curve is reduced, as the tails of the profile 109 are eliminated (the curve of intersection between a hypothetical plane and an observed specific anatomical region of the subject 107).

Since the FI and the BCS both represent synthetic indexes of fat reserves of the observed subject, it is possible to use the BCS value obtained from the formula (6) or FI value obtained from the formula (1d), (1e) and (1f) as a regressor, together with race, age and sex of the observed subject, to obtain a good approximation of the body weight.

This can be done by means of a polynomial regression on the basis of a reference group of subjects of known species, breed, sex, age and weight.

Therefore, once species, breed and sex are fixed, the weight turns out to be a function of age E and BCS B:

$$P = \xi(E, B) \quad (11)$$

An example of such function is represented by a polynomial regression having the following form:

$$\begin{cases} P_m = m_1 + m_2 E + m_3 E^2 + m_4 B + m_5 B^2 + m_6 EB + m_7 E^2 B + m_8 E^3 B \\ P_f = n_1 + n_2 E + n_3 E^2 + n_4 B + n_5 B^2 + n_6 EB + n_7 E^2 B + n_8 E^3 B \end{cases} \quad (11')$$

wherein the first formula is the weight $P_M$ of a male subject, age E and BCS=B.

The second formula is the weight $P_f$ of a female subject, age E and BCS=B.

Evidently the formulas (11) are specific for the species, breed and age group.

In the case of production animals, the crossings breeds should be treated as a breed per se.

The method for the determination of the parameters m, and n, of the regression is known in the literature and is based on the use of the weight, BCS, age, sex, race and species values of a group of reference subjects.

In the case of production animals, such as milking beef, the method proposed for the determination of FI, BCS and body weight, may be advantageously combined with the determination of estrus in order to determine a new index of the fertility state defined herein fertility index F.

In the intensive productions, indeed, fertilization occurs in almost all cases artificially (artificial insemination or FA). Since, as is known, the production of milk by a bovine is due to calving and that the milk production curve has its maximum in the first months after the calving and then decreases, the calving period must be reduced to minimum in order to maximize the productive performance.

However, the cow is fertile for a few hours, so it is essential to pinpoint the time of estrus in order to proceed with assisted reproduction in the moment of maximum chances of fertilization.

However, the chances of successful fertilization is not only dependent on the state of the subject's estrus, but also on its physical condition. In fact, it is known that a subject in poor physical condition is unlikely to be fertilized. There are numerous studies in the literature that demonstrate the correlation between the variations of BCS and fertility, for example in dairy cows. In summary, the existence of a body defense mechanism that prevents the conception of a new living being in the case in which the person has an inadequate physical condition is known. Probably this is due to the fact that in nature an inadequate physical condition, such as the extreme thinness (BCS between 1 and 2 in the scale of 1-5), is associated with the shortage of food resources in the environment, then to an extremely low probability for the mother to successfully conclude the pregnancy and the unborn to survive in the environment.

In intensive milk production, it is not uncommon to find very lean or very fat beef, or at least below or above the optimum body condition. This is due to many factors that distinguish a good by a poor breeding, but in any case due to the fact that the beef for the intensive production of milk have been genetically selected to produce huge daily quantities of milk in proportion to their body weight. This imply extreme precariousness of energy balance of the cattle, which must be maintained in a manner appropriate to the stage of lactation in which it finds itself, so that its energy balance is as more balanced as possible. However, an unfavorable relationship between feeding cost and milk selling price cost would make livestock uneconomical. So the breeder is constantly looking for the right balance between quality and quantity of feed, the state of livestock health and production of milk, often having to accept a certain degree of inefficiency in his process. In this context, a significant economic weight is constituted by the cost of semen doses for artificial insemination.

In summary, in the delicate economic balance of farms producing milk, failing an insemination means losing the seed value (often very expensive) and delaying of a month the launch of the milk production of that subject.

In the light of what has been illustrated, in order to maximize the probability of fertilization, it is substantial to observe both the state of oestrus and the body condition (BCS or FI) of dairy cattle.

There are a number of prior art techniques for the determination of estrus in dairy cattle which can be advantageously combined with the subject invention for the calculation of the FI and of the BCS. These solutions exploit behavioral traits or biological characteristics associated with the state of estrus. A few one are cited by way of example: the pedometers and the electronic collars, which detect the increase in motility of the subject; the so-called "tail painting" and its electronic versions, which detects the mounting reflex, induced by the state of estrus of a cow in her companions; the chemical analysis of milk, aimed at identifying specific chemicals associated with the state of estrus.

It is defined, in the present context, for a subject under oestrus, a fertility index F as the percentage change between the value of real $BCS_r$ and the value of the ideal $BCS_i$ of the subject in relation to its stage of lactation, according to the following formula:

$$F = E \cdot \frac{BCS_r}{BCS_i} \quad (12)$$

wherein E represents the state of oestrus (E=0 absence of oestrus, E=1 subject in oestrus), considering the BCS scale [1; 5], BCS, normally ranges in the interval [2.5; 3.5].

According to (12), the index of fertility F can assume the following values and meanings:
1. F=0, it indicates the absence of oestrus, regardless of the body condition;
2. F≅1, it indicates oestrus condition with optimal body condition ($BCS_r \cong BCS_i$);
3. F>1, it indicates a state of oestrus in "overcondition";
4. 0<F<1, it indicates a state of oestrus in "undercondition".

So if F has values in the neighborhood of 1, then the probability of successful insemination is maximum.

Figure 1:
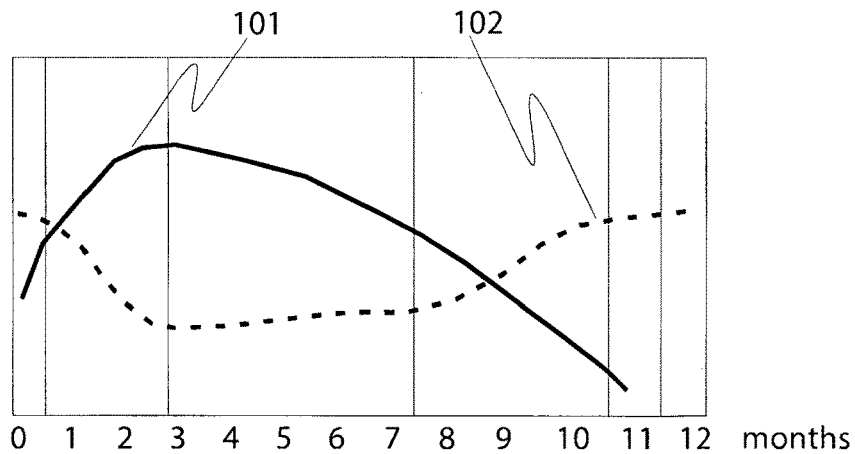

In FIG. 1 a prior art graph is shown in which the timeline is reported on the abscissa, wherein zero corresponds to the date of the last calving, the dotted line 102 represents the trend of the ideal BCS ($BCS_i$) and the continuous line 101 represents the trend of milk production.

A second configuration of the apparatus D subject of the invention can be used to make stationary plants of the automatic type. The apparatus D may advantageously be installed on top of those confined environments wherein the animals are to be closed for a short time for functional reasons, such as weighing, veterinary examination and/or administration of drugs, milking. In particular, the apparatus D can be used for the automatic measurement of the BCS within the containment box and/or weighing, within the milking robot, in the framework of milking parlors.

Figure 11:
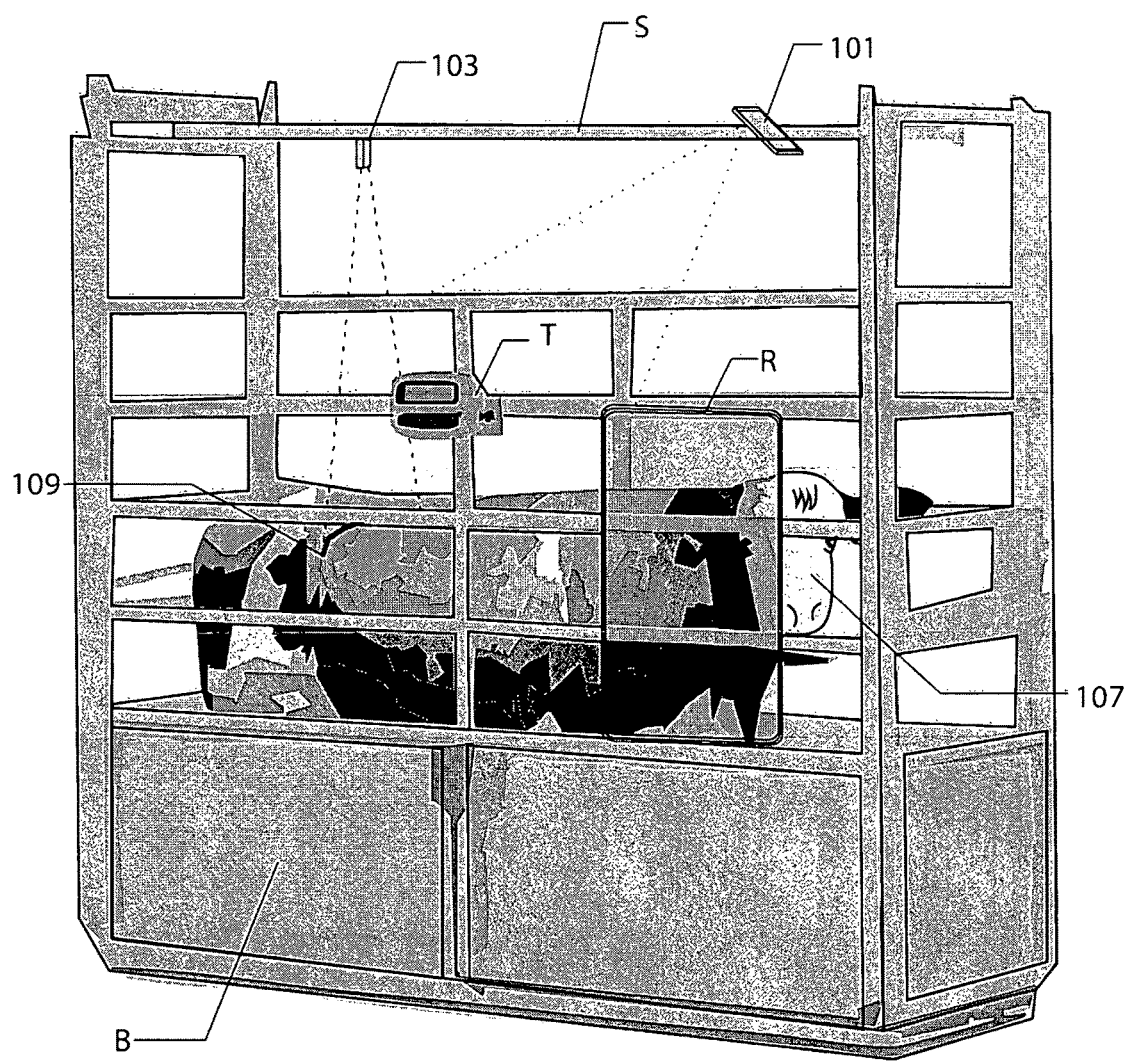
FIG. 11 shows a second embodiment of the apparatus of FIG. 5, of fixed automatic type applied in a weighing box.

By way of example of such a second configuration, let us consider FIG. 11, wherein the installation of the apparatus D inside a weighing box B for cattle is shown schematically. The same methodology is applicable in any other kind of condition in which the subject 107 is locked in a known position. This will allow positioning the control unit 101 in such a way to frame optimally the region of the anatomy (e.g. lumbar region) of the observed subject 107, in which the profile 109 is highlighted by means of one of the described methods. The acquisition command of the image, or image sequence, can be given manually by a technician using a remote control, which would play the function of the button 106. In the alternative, if a front and/or rear gate are present, limit switches can be used which allow the control unit to identify the moment in which the animal is actually present to inside the box. For this purpose other types of presence sensors can advantageously also be employed, such as infrared, microwave, ultrasonic sensors, RFID readers in the case where the animal is equipped with transponders for the electronic identification. With the same objective, inside the control unit, an application of motion detection can be implemented which allows detecting the presence of an animal, automatically determining the optimum time for the acquisition of the image.

In the same way, the identification of the animal may be performed manually by the examiner by means of a remote terminal that is radiofrequency interfaced to the control unit 101. In the alternative, in order to automate the process, the control unit 101 can be interfaced to an RFID reader indicated in the figure with the letter R. A further possible alternative applicable in the field of piebald animals or animals provided with a marking on the back, consists in the implementation of a software application for automatic recognition of such stains and/or markings, recorded by the camera 102, in order to uniquely identify the subject 107.

In this second configuration, the apparatus D can be interfaced with other measurement instruments present therein, such as the weighing terminal T for the simultaneous recording of the weight of the animal 107, the milk meter in the case of the milking robots, the system for estrus detection, other remote terminals for recording, by veterinarians and/or technicians, the administered drugs and/or performed prophylaxis and/or any other kind of useful examination or note.

In the same control and processing units of the herein proposed system an algorithm can be advantageously integrated for the recognition of the state of oestrus of the observed subject, by means of the tail painting method. As it is known such a method consists of painting the tail of a cow with a suitable fluorescent paint. At the time when that individual is in estrus, the covering reflex is induced in the companions, which causes in the observed subject an abrasion of the caudal region. Such abrasion determines the partial or total removal of previously applied paint. This change is detectable by means of the same video-recording apparatus 102 used for the detection of the profile 109.

Figure 12:
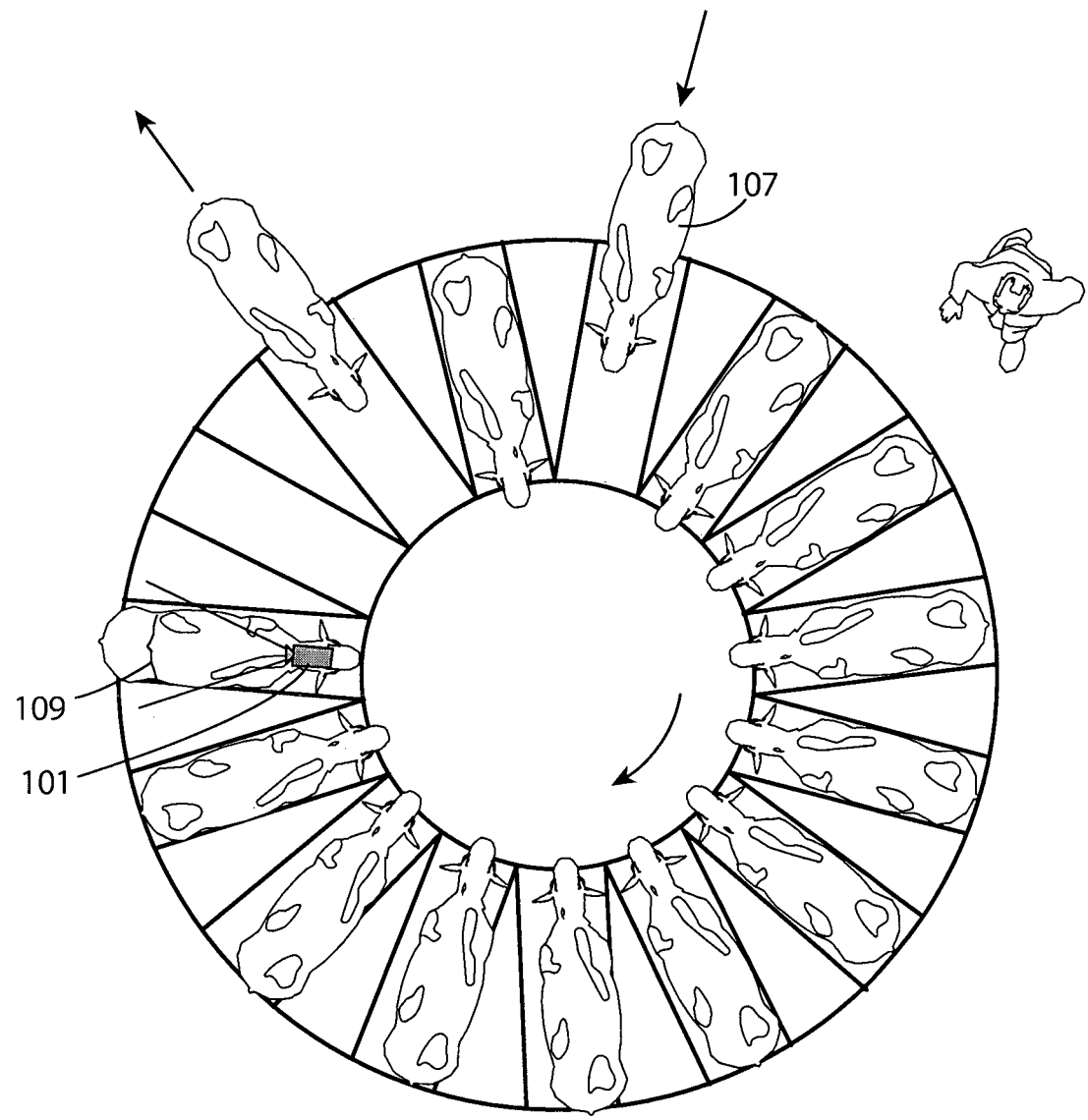
FIG. 12 shows the same second embodiment of the apparatus of FIG. 5, of fixed automatic type applied in a rotating-type milking parlor.

With reference to FIG. 12, the second configuration of the apparatus D can be installed in the rotary milking parlor. This implies, as already illustrated in FIG. 11, that said control unit 101 and said camera 102 (for example integrated in the control unit 101) is positioned on a support placed upward with respect to the observed subject 107, on which at least a profile 109 has been highlighted, by means of one of the described methods.

In this type of milking parlor the animals run on a sort of carousel, so that, by fixing the apparatus D hanging from the ceiling, as shown in FIG. 12, all animals will pass under it, in a known position, before exiting the carousel. An automatic trigger (e.g. photoelectric switch, mechanical switch, proximity sensor) will play the function of the button 106 illustrated in FIGS. 6a and 6b, communicating to the control unit 101 the optimal time in which the acquisition of the image is to be run by means of the camera 102. Also in this case, all the animal identification solutions and solutions of interfacing to other systems and the technician are applicable already illustrated in the case of installation within the weighing box (first configuration).

A third configuration of the apparatus D object of the invention can be used to make movable systems of the automatic type. Indeed, the apparatus D can be mounted on an air guideway which operates its automatic handling inside a milking parlor. This configuration is applicable to any kind of room (e.g. herringbone, parallel).

Figure 13:
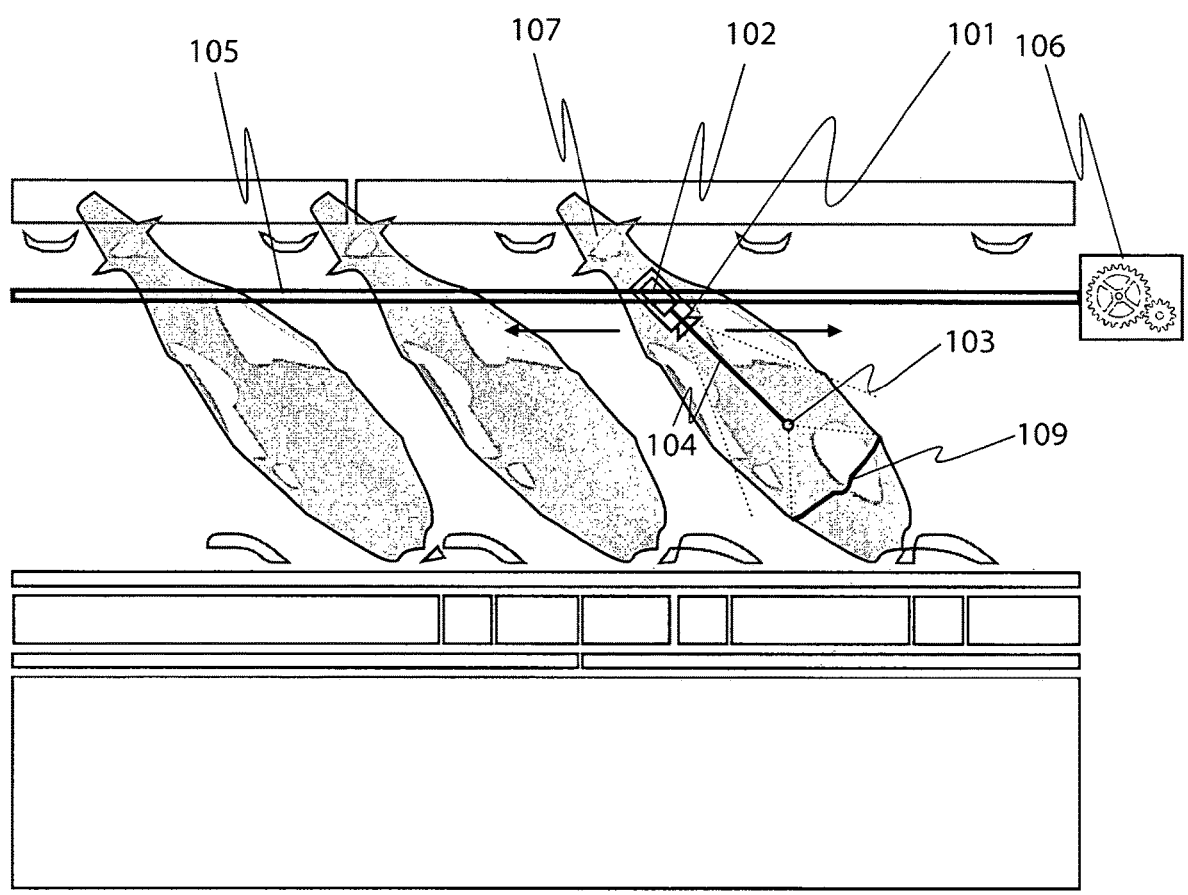
FIG. 13 shows a third embodiment of the apparatus of FIG. 5, of the automatic type, movable on aerial guideway in an angular milking parlor.

By way of example of such a third configuration of the apparatus D, let us consider FIG. 13, in which the apparatus D subject of the invention is installed in a milking room of the "herringbone" type. In this room, during the stage of milking, the animals are stuck in known positions. In this context the control unit 101 may be advantageously suspended on a air track 110, together with said camera 102. In this configuration, the apparatus D is moved along the air guideway 110 by the motor 111 by means of suitable motion transmission elements (e.g. belt, chain, screw) and receives the release command of photography by means of suitable automatic trigger (e.g. photoelectric sensor, mechanical switch, proximity sensor) that performs the function of the button 106 illustrated in FIGS. 6a and 6b, communicating to the control unit 101 the optimal time in which the image is to be captured during the movement along the guideway. The triggers must be positioned in correspondence of each animal. The shutter speed of the camera 102 and the lighting system of the room must be appropriate to the speed at which one intends to move the device D, so that the images look sharp and well exposed. Same solution is applicable to any other kind of the milking parlor (e.g. "parallel" type).

Also in this third configuration, all the animal identification solutions and solution for interfacing to other systems and to the technician may be advantageously applied, which have been already described for the previous and configurations.

Figure 17:
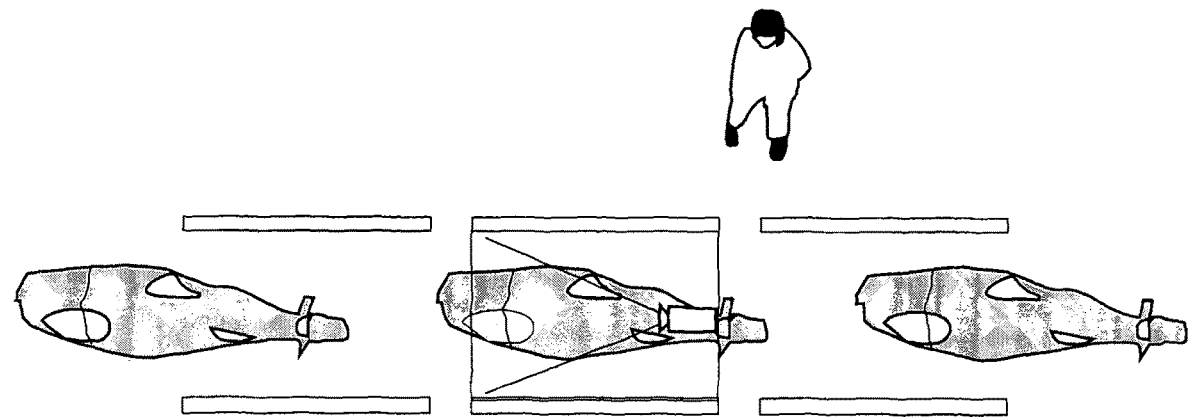
FIG. 17 shows a fourth embodiment of the apparatus of FIG. 5, of the gap static automatic type, the gap being freely crossable by animals.

With reference to FIG. 17, a fourth possible configuration consists in realizing a passage traversable by animals. By suitable proximity sensors of the type described in the previous configurations and/or by appropriate electronic systems for identifying animals of the type described in the previous configurations, one can determine the actual position of the animal in transit through the gap. In this way, it is possible to determine the optimal time at which the picture is taken by means of the photographic apparatus, so as to record the anatomical region subject of the evaluation, which has been highlighted on the profile 109, on a plane transverse to the spine, using one of the described methods, as illustrated in FIG. 17.

Even in this fourth configuration, all the animal identification solutions and solutions for interfacing to other systems and to technician may be advantageously applied, which have been already described for the previous configurations.

Figure 21:
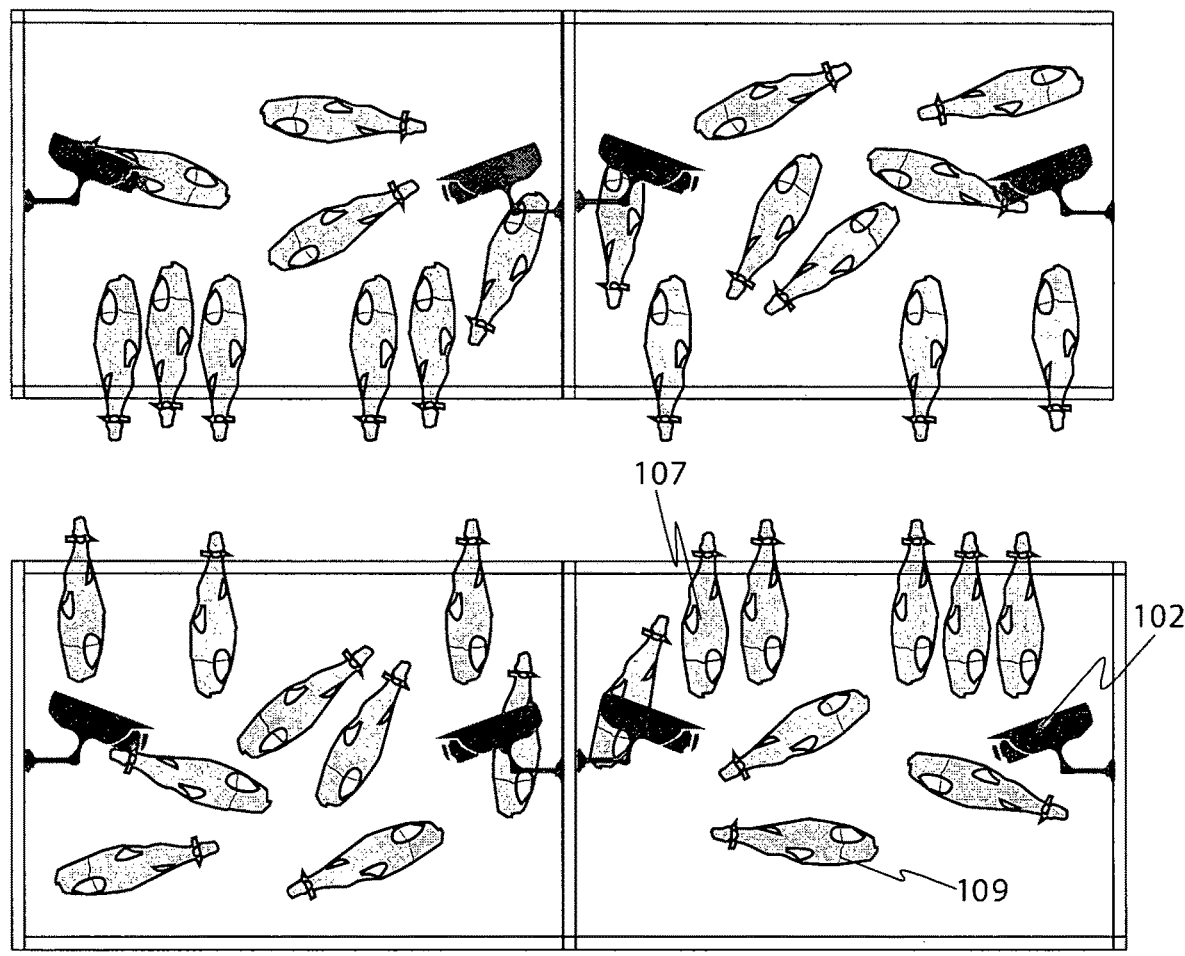
FIG. 21 shows a further embodiment of the apparatus of FIG. 5, of static automatic type, obtained by positioning a suitable number of high-resolution cameras above the animal housing box.

With reference to FIG. 21, a fifth possible configuration consists in placing appropriate high-resolution cameras 102 above the animals stabling boxes 107, in order to be able to record, with default time rate, the animals, on which the profile 109 has been highlighted by one of the described methods.

The method and the apparatus D described above can be also used to assess the BCS of a deceased animal (e.g. post-mortem along the slaughter line), in order to classify its carcass, and in any case of non-entire animal.

Figure 14:
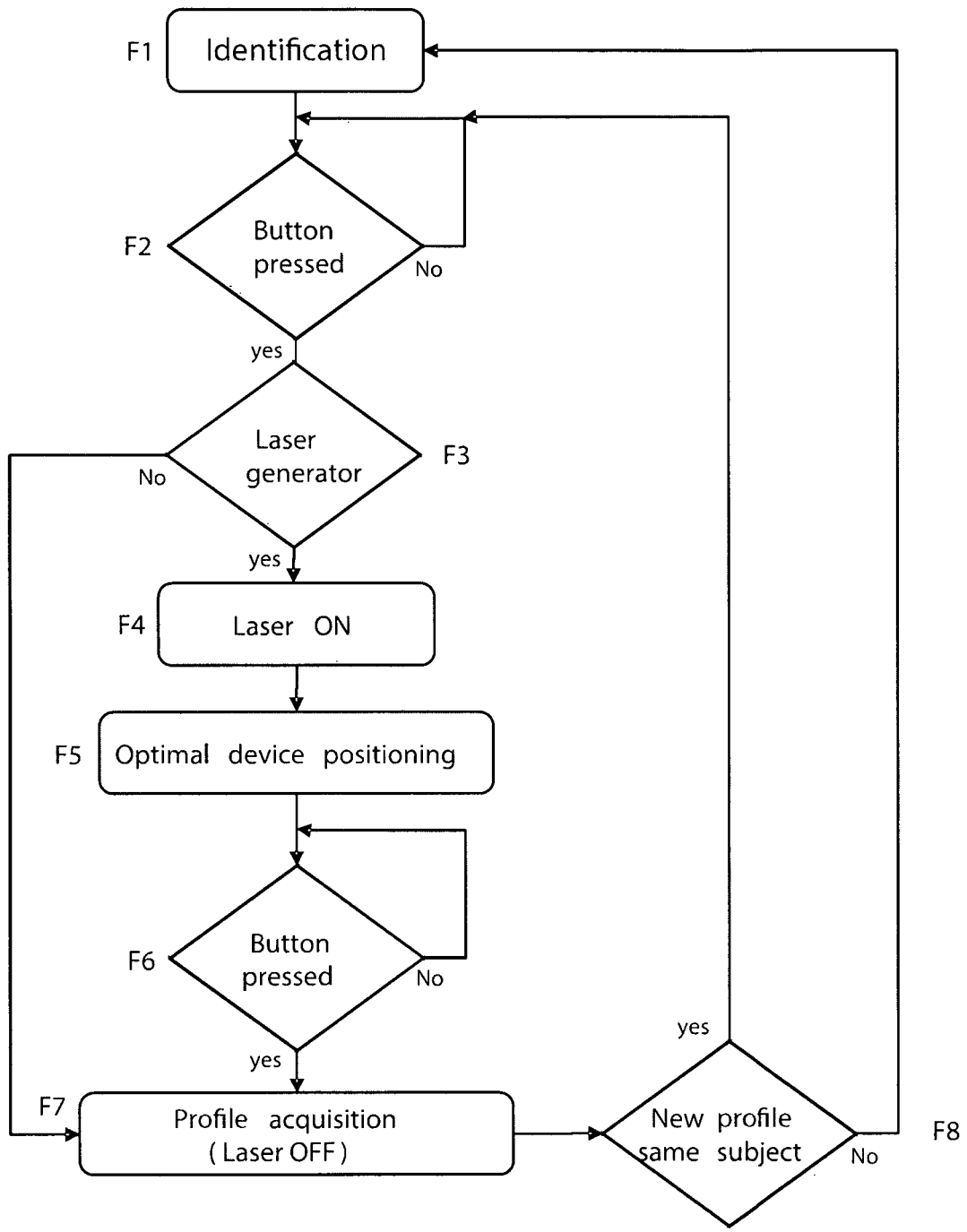
FIG. 14 shows a block diagram relating to the acquisition and control functions in the first embodiment of the apparatus of the invention.
Figure 15:
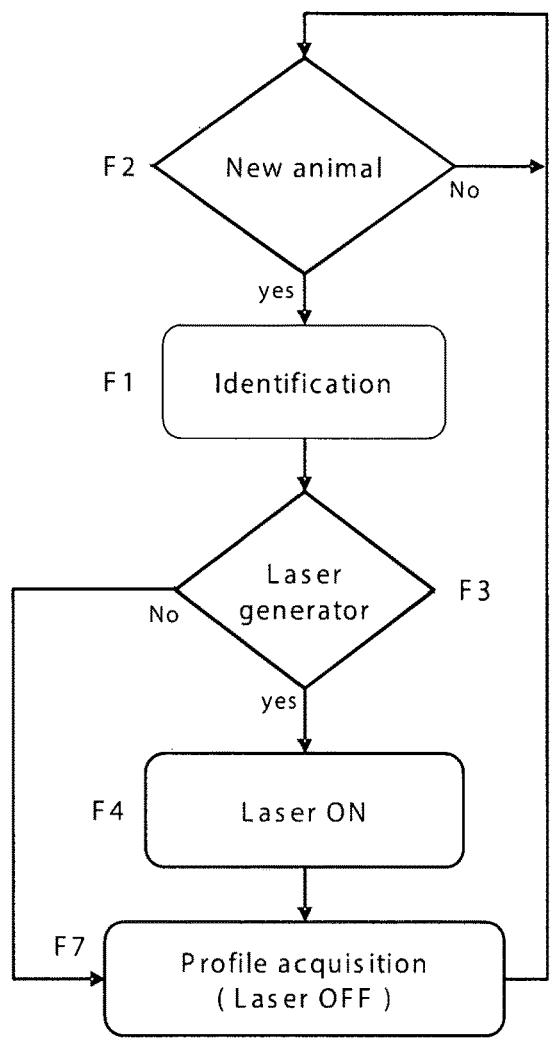
FIG. 15 shows a block diagram relating to the acquisition and control functions in she second and third embodiment of the apparatus of the invention.
Figure 16:
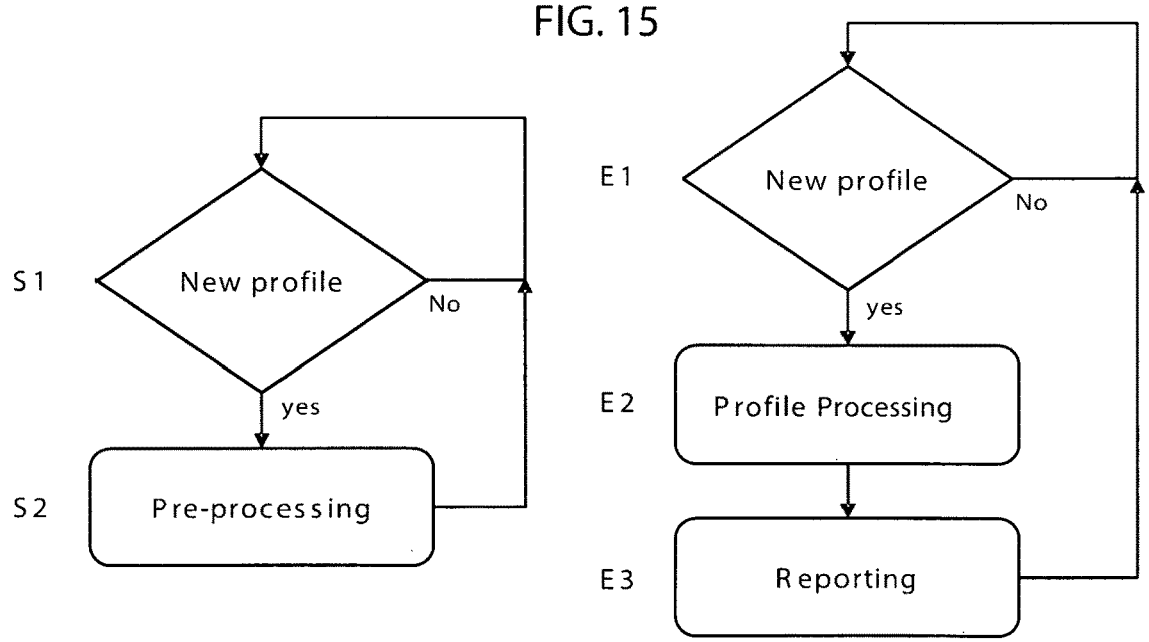
FIG. 16 shows a block diagram relating to the functions of pre-processing and processing present in all embodiments of the apparatus of the invention.

Referring to FIGS. 14, 15 and 16, the functions of acquisition, control, pre-processing and processing are illustrated both in the case of manual configuration and in the case of automatic configuration.

In particular, reference is made to FIG. 14, concerning the portable tool manually controlled by a technician, according to the first configuration of the apparatus D. Before carrying out the measurement of the BCS, the technician 108 performs a step 1 which consists in the identification of the subject 107 to be examined, manually recording a new individual data record in the data processing unit E or by manually selecting the subject within a database comprised in said data processing unit E. This process can be accelerated by the implementation of a voice interface in the control unit 101 based on the prior art solutions such as the ASR (Automatic speech Recognition) and TTS (Text to speech). In this way, the technician can identify the animal by uttering the last digits of the identification ear mark or the digits of the company number associated to the animal, or even saying the name of the animal. Obviously these data must have been preloaded into the integrated database in the control unit 101, which, once the voice control is decoded, can give confirmation to the technician by means of the TTS (text to speech).

This identification process can be automated by means of electronic identification devices such as subcutaneous transponders or electronics ear tags or endoruminal electronic boluses or electronic pedometers or electronic collars and the like. Indeed, in the case wherein the examined animal 107 is equipped with one of these electronic radiofrequency identification tags, the technician 108 can identify it by means of a portable reader of RFID (Radio Frequency iDentification) type, e.g. connected by suitable wiring, or via bluetooth or Wi-Fi with the control unit 101 or integrated in said control unit 101.

In this way, identification step F1 would be easy and rapid.

The technician 108 at this point presses the button 106. The process F2, as soon as the pressure of the button is detected, executes step F3 of verification of the presence of a laser generator. Where such a laser generator is present in the system, then step F4 of ignition of said laser generator is carried out. The technician, with the help of the projection of the laser plane visible on the back of the animal, shall carry out the step F5 of optimal positioning of the apparatus D with respect to the observed subject 107, in order to record the morphological character used for the determination of the FI and the BCS (e.g. lumbar profile). At a time when the technician has identified the optimal position, he/she presses again button 106. This action is detected by the process F6 which will perform the step F7 of image acquisition and laser switching off.

In the case wherein no laser generator is present in the system, for example because the profile 109 has been highlighted by other technique among those described, the technician 108 will simply press a single time the button 106. This action causes the execution of the acquisition step F7.

If the technician wants to acquire more photos of the same subject, then the process starts again from step F2, otherwise it provides for the identification of a new animal going back to step F1.

In the case in which the instrument is of a portable type according to the first configuration, the technician 108 places himself/herself before or rearward with respect to the subject 107 and positions the apparatus D so as to record the profile 109, highlighted by one of the described methods. The placement of the technician 108 in front of the observed subject 107 appears particularly advantageous, possibly while this is eating, because in this condition, said examiner 108 can perform the measurement safely, keeping in the "clean area" of the stable, outside the animals' containment box.

The apparatus D appears to be robust to the subjectivity of the technician in his positioning in terms of height and inclination with respect to the observed subject 107.

Reference is now made to FIG. 15, relevant to the fixed tool in automatic configuration, according to the second and the third configuration of the apparatus D.

The step F2 consists in the detection process of a new entity 107, by means of at least one of the sensors described in the first and second configurations.

The second configuration provides that the apparatus D is fixed and that the animal 107 moves until it reaches the measurement position, the third configuration provides that the animals are fixed at known positions and the apparatus D moves in the optimal measurement positions, the fourth configuration provides that the animals freely pass through the gap along a direction, while the fifth configuration provides that the animals will move freely in the control area of the system.

In these five configurations, the detection of the presence of a new animal can be carried out manually by the examiner by means of a remote control, which would play the function of the button 106 or automatically by means of suitable hardware or software sensors. For example, where front and/or rear containment gates are present, limit switches can be used which allow the control unit 101 to determine the moment in which the animal is actually in the measurement position. For this purpose, other types of presence sensors can advantageously also be employed, such as infrared, microwave, ultrasonic, mechanical sensors, RFID readers where the animal is equipped with transponders for the electronic identification. With the same objective, an application of motion detection can be implemented within the control unit, which allows detecting the presence, the position, orientation and direction of movement of the animal, automatically determining the optimum time for the acquisition of the image.

Once detected the presence of a new subject in the measurement position, the system goes to step F1 of the subject identification. The identification process can be sequential and synchronous with the other steps of analysis or fully asynchronous and separate. In both cases, the control unit 101 will need the results of the identification process.

This identification process can be executed according to various prior art techniques: manually by the technician by a remote terminal connected by cable or wireless to the control unit 101. Alternatively, in order to automate the process, the control unit 101 can be interfaced to an RFID reader, where the animal is equipped with an electronic identifier. Further possible alternative applicable in the case of piebald animals or equipped with a marking on the back, consists in the implementation of a software for the automatic recognition of such stains and/or marks, in order to uniquely identify the animal.

Once the subject is detected and identified, where is present a laser generator (step F3), the system provides to switch on said laser generator (step F4) and to acquire at least a profile (step F7).

Once this sequence is completed, the system goes back to the process of presence detection in step F2.

The processing process can take place even in the absence of identification of animals, where the interest is to calculate an average FI and/or an average BCS of a group of animals.

FIG. 16 shows the pre-processing and data processing processes.

The pre-processing is preferentially implemented in the control unit 101, which, once a new profile is available (step S1) provides for the encryption of all the data (e.g. data of the animal, data collected by sensors, data collected by other connected measuring systems, data entered by a technician, taken photography or sequence of photos), their coding inside of a single data packet compressed according to prior art techniques (e.g. watermarking techniques) and their forwarding towards the remote processing unit or the local processing process (step S2).

The process of elaboration of the data is preferably implemented in a central remote unit (processor), with all the characteristics of computing power, memory, redundancy, business continuity, disaster recovery, etc. which ensure the processing speed and security of the data.

This process is constantly waiting for new data to be processed (step E1). In the moment in which a new packet is received by a control unit 101, the central system (which contains at least one processor) executes its processing (step E2) according to the following steps:

extraction, decompression and decryption of the data contained inside the received packet,
 data consistency check,
 application of the process described in FIG. 10 or other similar process for the determination of the points of tangency of the curve 109,
 application of at least one of the formulae (1d), (1e), (1f), (1g) for the determination of FI,
 application of the formula (8) for the determination of the BCS for the specific breed, application of the formula (11) for the determination of the weight, application of the formula (12) for the determination of fertility, storing information in the appropriate tables of the central database.

After being processed, the data can be made available to the user (step E3) (e.g. transmitted to the device D and/or transmitted to another database and/or published on a web page).

The region of the lower back L, abdominal A, sacral S, femoral F, pectoral P, gluteal G and dorsal D, depending on the species, are particularly significant for the purposes of evaluation of the BCS, in their median part M, since it is in such regions that the fats are primarily accumulated in the case of greater availability and they are mobilized faster in conditions of necessity. The best evaluation of FI by the formulas (1d), (1e) and (1f) and the BCS by formula (8) is thus obtained by highlighting, using one of the described methods, the profile 109 in its central region.

In general, the profile 109 tends to change shape, to shift from said middle region M.

In the case of the lumbar region in dairy cattle, it was observed that displacements forward or backward from the optimal position, still within the lumbar region, produce small variations in the FI and the BCS, which are little influential in estimating the BCS for the common use.

Figure 22:
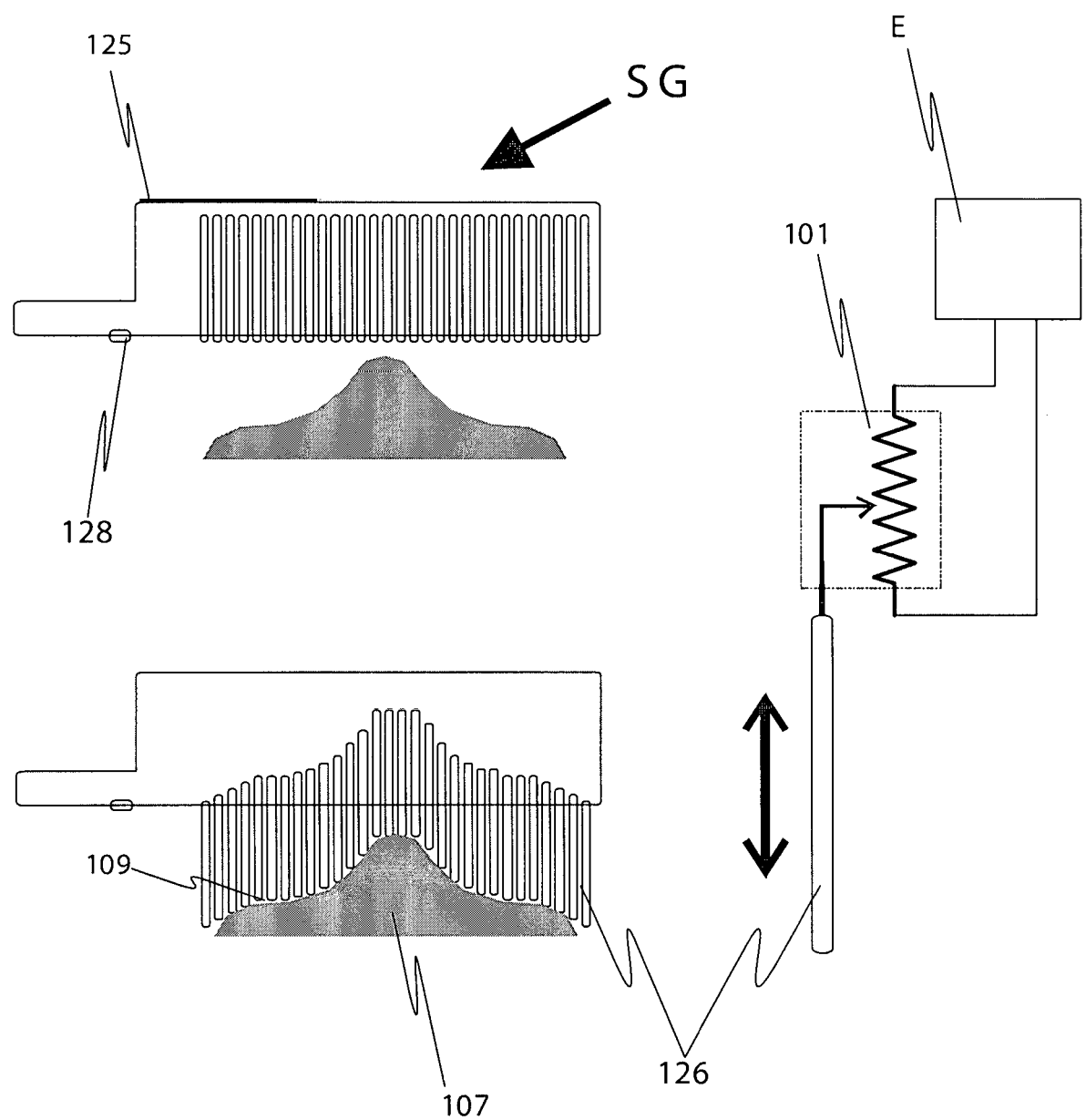
FIG. 22 shows a further embodiment of the apparatus of FIG. 5, of static manual type, wherein the profile is acquired by means of a specific comb profilometer of the electronic type.

With reference to FIG. 22, a further apparatus PG is proposed for the implementation of the method according to the present invention. This apparatus consists of a perfected electronic needle profilometer comprising a number of needles 126 parallel to each other and movable in a direction, at least one digitizing system for digitizing the position of said needles 127, at least a data processing unit E, at least one peripheral user interface 125. Such apparatus PG includes a physical contact between the instrument and the animal, unlike the apparatus D that instead performs non-contact measurements.

In the moment when this perfected needle profilometer PG is rested on an anatomical region of the animal 107, it will describe the profile 109 with a resolution proportional to the number of needles used. The control unit 101 converts the dislocation of said needles into an electrical signal processable by a local or remote data processing unit E.

Figure 23:
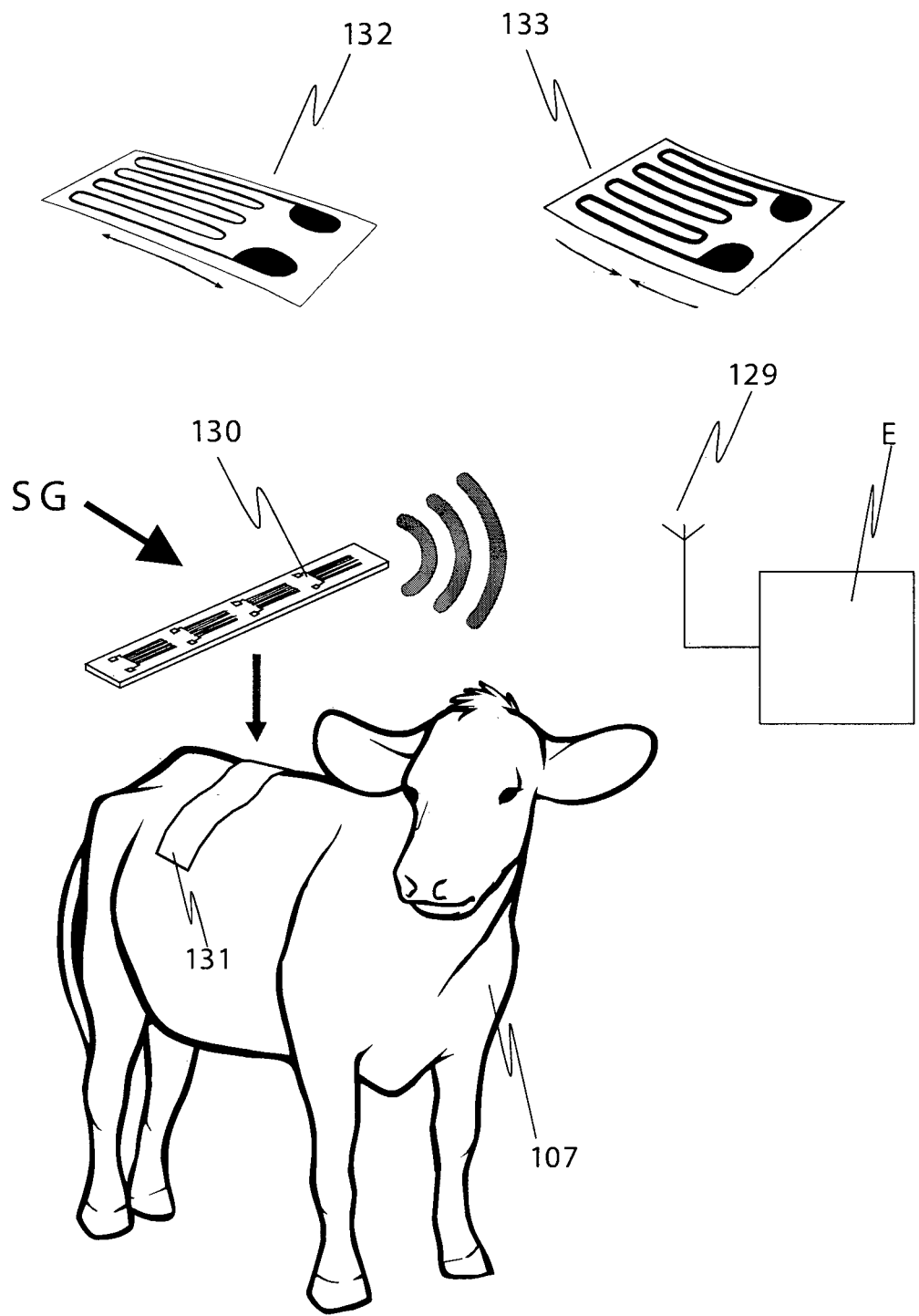
FIG. 23 shows a further embodiment of the apparatus of FIG. 5, of the automatic dynamic type, wherein the profile is acquired by means of an adhesive strip equipped with a set of electronic-type flex sensors.
Figure 24:
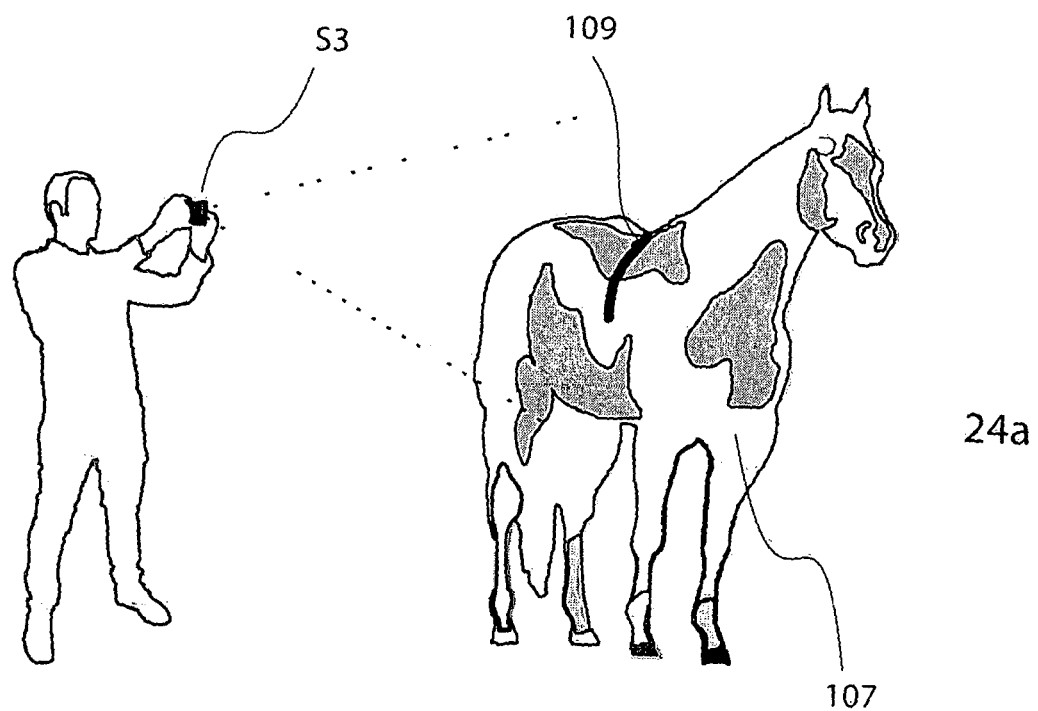
FIG. 24 shows a further embodiment of the apparatus of FIG. 5, wherein the profile is acquired by means of a three-dimensional scanner, for example of the time of flight (TOF) type.
Figure 24:
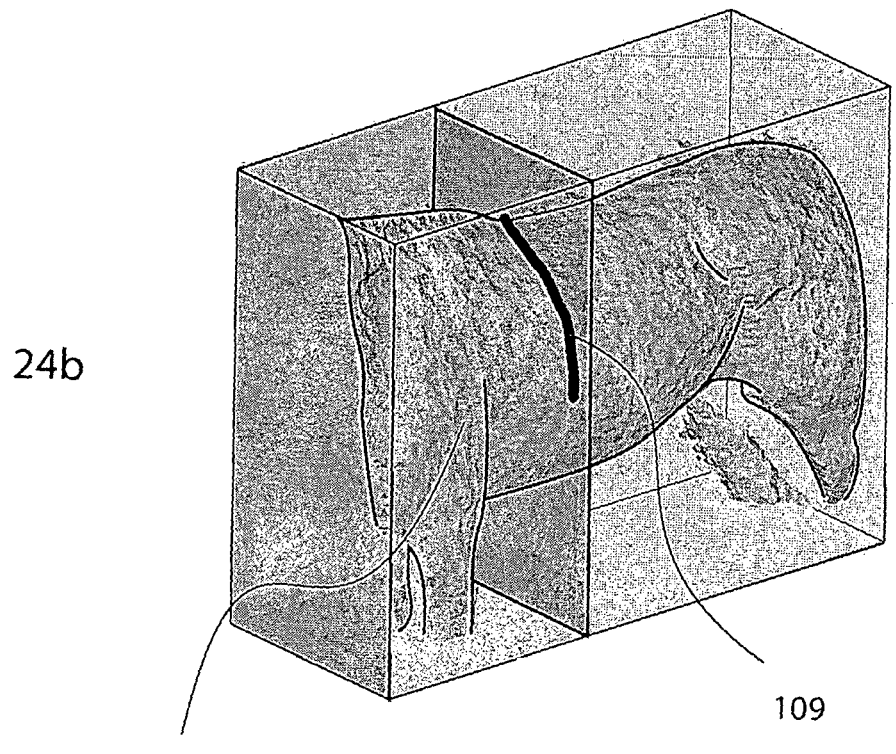

With reference to FIG. 23, a further apparatus SG for determining the body condition score of an animal 107 is proposed. Such apparatus comprises at least a flexure-sensitive band 131 composed of a suitable number of electronic strain gages 130, at least one digitizing system of the signal produced by said strain gauges, at least a data processing unit E, wherein said flexure-sensitive band 131 is applicable on the surface or under the skin of the observed subject.

Such apparatus, by means of electronic strain gauges 130, is able to detect the dilatation 132 or compression 133 along the direction perpendicular to the animal's spine 107, in order to describe the profile 109 with a resolution proportional to the number of strain gages integrated in said band 131.

These electronic strain gauges are connected, via cable or wireless, to a data processing unit (E), local or remote, capable of extracting a profile 109 processable according to the techniques already described.

With reference to FIG. 23, a further apparatus S3 is proposed for the implementation of the method according to the present invention. This apparatus consists of a three-dimensional scanner, according to known technique, for example of the TOF (time or flight) type, connected to a control unit. Such assembly allows acquiring the profile 109, which is processed by a processing unit of in order to obtain the index FI, the BCS, the estimated body weight and the index of fertility, as already described.

Experimental Tests

Here follows a comparison table between the BCS evaluated by an experienced veterinarian and that of the system in two separate test sessions on the same group of animals.

| Farm N. | Test | System | Expert Vet | Test | System | Expert Vet |
|---------|------|--------|------------|------|--------|------------|
| 106 | A | 3.1 | 2.75 | B | 2.9 | 3.00 |
| 146 | A | 3.2 | 3.50 | B | 3.2 | 3.25 |
| 148 | A | 2.9 | 2.75 | B | 3.0 | 3.00 |
| 150 | A | 3.2 | 3.00 | B | 3.1 | 3.25 |
| 161 | A | 3.0 | 3.00 | B | 3.2 | 3.00 |
| 204 | A | 2.8 | 3.00 | B | 2.8 | 3.00 |
| 210 | A | 2.7 | 2.75 | B | 2.7 | 2.75 |
| 241 | A | 2.9 | 3.00 | B | 2.8 | 3.00 |
| 243 | A | 2.6 | 2.50 | B | 2.7 | 2.50 |
| 267 | A | 3.0 | 3.00 | B | 3.0 | 2.75 |
| 270 | A | 2.3 | 2.50 | B | 2.3 | 2.50 |
| 290 | A | 2.7 | 2.50 | B | 2.7 | 2.75 |
| 321 | A | 3.7 | 3.75 | B | 3.6 | 3.75 |
| 365 | A | 3.0 | 3.00 | B | 2.8 | 2.75 |
| 394 | A | 2.9 | 2.75 | B | 2.8 | 3.00 |
| 427 | A | 2.8 | 2.50 | B | 2.8 | 2.75 |
| 505 | A | 3.3 | 3.25 | B | 3.3 | 3.00 |
| 512 | A | 2.8 | 2.75 | B | 2.8 | 2.50 |
| 529 | A | 2.2 | 2.50 | B | 2.2 | 2.25 |
| 565 | A | 2.6 | 2.75 | B | 2.7 | 2.25 |
| 580 | A | 3.2 | 3.25 | B | 3.2 | 3.25 |
| 584 | A | 3.3 | 3.50 | B | 3.5 | 3.50 |
| 595 | A | 3.3 | 3.25 | B | 3.2 | 3.25 |
| 600 | A | 2.8 | 2.75 | B | 2.8 | 2.75 |
| 609 | A | 3.2 | 3.00 | B | 3.3 | 3.00 |
| 661 | A | 3.2 | 3.25 | B | 3.2 | 3.50 |
| 664 | A | 2.8 | 3.00 | B | 3.0 | 3.00 |
| 704 | A | 3.1 | 3.25 | B | 3.1 | 3.25 |
| 758 | A | 3.4 | 3.25 | B | 3.3 | 3.25 |
| 786 | A | 3.3 | 3.25 | B | 3.5 | 3.50 |
| 835 | A | 2.7 | 2.75 | B | 2.8 | 2.75 |
| 836 | A | 3.6 | 3.75 | B | 3.8 | 3.75 |
| 846 | A | 2.8 | 2.75 | B | 2.8 | 2.50 |
| 854 | A | 2.3 | 2.25 | B | 2.3 | 2.50 |
| 881 | A | 2.7 | 3.00 | B | 2.8 | 3.00 |
| 962 | A | 3.2 | 3.00 | B | 3.3 | 3.00 |

This test was performed in the "double-blind" way on subjects of Holstein race in two test sessions (A and B), recording the determination made by an experienced veterinarian and processed by the system in question according to the formula (8). The first column shows the company's identification number of the animals, in the third and the sixth column show the values of BCS estimated by the system in the two tests A and B, the fourth and seventh column list the opinions expressed by the veterinary expert. As it is shown, the system shows a very high repeatability in the determination of the BCS on the same subjects. Moreover, in 85% of cases, the difference between the judgment of the system and that of the evaluator is less than a quarter of a point.

Some New Features Over the Prior Art

The apparatus D and the method subject of the present invention presents some substantial peculiarities with respect to the known art.

In particular, the method of determining the FI and the BCS and its application tools allow to automatically perform the assessment of body condition of an animal, overcoming in a definitive way the problem of subjectivity in visual evaluation by an evaluator and at the same time reducing the degree of complexity of the examination in such a way to make the method applicable to simple and portable instruments.

In addition, in the case of portable application, the proposed system reduces significantly (5-10 seconds) the detection time and the BCS evaluation with respect to any other portable or visual inspection method. In the case of fixed system, equipped with electronic device for identification of the animals, the analysis time is reduced to the photo shutter time of a camera (shutter time of an order of magnitude equal to fractions of a second).

In the case of portable application for the measurement of the BCS in cattle, in contrast to the common practice of observing the animals rearward and then inside the animal containment box (dirty area), the technician can perform the measurements by positioning him/herself in front of the animal, outside the boxes.

Is particularly advantageous to use the tool while the animals eat with the neck trapped in the containment fence. In this way the technician, remaining in the feed corridor, i.e. in the clean area, can carry out the detection of the BCS of all "stuck" animals in a rapid sequence, in maximum safety and minimizing the time required for the measurement of the whole herd.

Furthermore, in the case of a portable application, the proposed system appears to be robust to the possible positioning errors relating to the observed subject and the skeletal variations between individuals having the same body condition.

This makes the system substantially independent from the skilled technician who uses it. Changes in the position of the measuring system relative to the observed subject, such as tilt and height, do not influence in a significant way the value of the BCS. The higher skill influences only the speed of acquisition.

In the case of application combined with an electronic identification system for the identification of the observed subject, the acquisition speed further increases.

In case of application on animals with piebald coat or provided with a marking that rend them visually recognizable (e.g. a code printed on the back), the proposed system can advantageously use methods of image processing to identify the animal on the basis of one image, simplifying and further speeding up the measuring process.

The proposed method can be applied both in portable type tools and in stationary-type solutions. In particular, it can be advantageously installed in a stationary manner with automatic operation in any milking parlor, milking robot, weighing or animals containment boxes, passing corridor and stabling box.

The proposed method can also be applied to air detection, for example, installed on board a drone or n-copter.

In the area of monitoring of herds, such a solution can be advantageously combined with other visual and/or morphometric and/or biometrics solutions of identification the animals.

An important novelty of the invention consists in the independence of the method and its body condition index FI with respect to species, breed, sex, age and absolute size of the observed subject.

Another novelty of the invention lies in its ease of implementation, robustness to environmental changes, substantial independence from the capacity of the user, its applicability in portable solutions. These characteristics make the invention particularly suited to the application context of a stable.

In the present invention, moreover, only a morphological trait (profile) is evaluated in a specific way, the veterinarian considers 5 or more of them. By accurate mathematical correlation, the invention is able to reduce the number of assessments.

The proposed method also has the advantage over the known prior art to be able to be implemented even on simple devices (e.g., smartphones) without need for additional equipment. This is a direct consequence of the fact that the method of the invention analyzes the profile 109 irrespective if its absolute physical size.

In the foregoing, preferred embodiments have been described and variants of the present invention have been suggested, but it is to be understood that those skilled in the art can make modifications and changes, without so departing from the related scope of protection, as defined by the appended claims.

CLAIMS

1) Method for determination of an numeric index indicative of the energy reserves in the form of fat stored by an animal (107) dead or living of any species and race, including humans, for example the body condition score or the body mass index, wherein the following steps are performed:

A. digitally detecting, by means of optical detection of reference elements, applied or projected on the body of the observed subject, or by another type of detection system, with contact or without contact, of at least a profile (109) of an anatomical region of morphological interest, said at least a profile being defined as the shape of the curve that describes at least part of the outer perimeter of a section of said anatomical region, such a curve lying on an imaginary plane intersecting said anatomical region;

B. sending said at least a profile (109) of the step A to at least one data processing unit (E);

C. Calculating a numerical index R indicative of the energy reserves in the form of fat accumulated by the animal, in particular in said anatomical region, by at least a data processing unit (E) on the basis of said at least a profile (109) of step A; and D. correlating, in said at least one data processing unit (E), by means of a predefined mathematical transform, said numeric index R with one or more state features of said animal;

wherein on the body of the animal a first side (LS or RS) of said anatomical region with respect to the backbone of the animal (S) is present or a first side and a second side (LS, RS) of said anatomical region with respect to the spine (S) of the animal are present, and wherein said profile includes a point of relative maximum $P_M$ on the spine of the animal and a first development of the profile (109L or 109R) on said first side or a first and a second development of the profile (109L and 109R) respectively on said first and second side (LS, RS), The method being characterized in that step C includes the following sub-steps:

C1. individuating the coordinates of the relative maximum point $P_M$ of said profile;

C2. determining a first straight line ($\beta$) tangent to said profile (109), said first straight line starting from the relative maximum point $P_M$ and touching said profile at a first point of tangency $P_1$ of said first side, or in addition to the first straight line of tangency determining also a second straight line of tangency ($\alpha$) running from the point of relative maximum $P_M$ and touching said profile at a second point of tangency $P_1'$ on said second side;

C3. in the case in which in step 2 only said first tangent point $P_1$ has been calculated, taking as the second development (109L, 109R) of said profile the specular projection of said first development with respect to the direction of the spine, and assuming as the second point of tangency $P_1'$ the point specular to said first point of tangency $P_1$ with respect to the direction of the spine;

C4. calculating a first broken line point $P_2$ and a second broken line point $P_2'$ as the intersection between said profile and a straight line ($\gamma$) parallel to a base segment which goes from $P_1$ to $P_1'$;

C5. calculating said numeric index R as:

$$R = f(\alpha_1, \alpha_2, \alpha_1', \alpha_2')$$

wherein $\alpha_2$ is the angle between the segments $\overline{P_M P_2}$ and $\overline{P_2 P_2'}$, $\alpha_1$ is the angle between the segments $\overline{P_2 P_1}$ and $\overline{P_1 P_1'}$, $\alpha_2'$ is the angle between the segments $\overline{P_M P_2'}$ and $\overline{P_2' P_2}$, $\alpha_1'$ the angle between the segments $\overline{P_2' P_1'}$ and $\overline{P_1' P_1}$, and wherein $\alpha_2 = \alpha_2'$ and $\alpha_1 = \alpha_1'$ in case of the assumption of step C3 has been made.

2) Method according to claim 1, wherein in step C5 first a synthetic index $R_L$ relevant to said first development (109L) and a synthetic index $R_R$ relevant to said second development (109R) are calculated as $$R_L = f(\alpha_1, \alpha_2), R_R = f(\alpha_1', \alpha_2')$$

and then:

$$R = \frac{R_L + R_R}{2}$$

3) Method according to claim 1 or 2, wherein:

$$R = f(\overline{\alpha_1}, \overline{\alpha_2})$$

or $$R = f\left(\frac{\alpha_2 + \varphi}{\alpha_1 + \varphi}, \frac{\alpha_2' + \varphi}{\alpha_1' + \varphi}\right)$$

or:

$$R_L = f\left(\frac{\alpha_2 + \varphi}{\alpha_1 + \varphi}\right), R_R = f\left(\frac{\alpha_2' + \varphi}{\alpha_1' + \varphi}\right), R = \frac{R_L + R_R}{2}$$

or:

$$R = f\left(\frac{\overline{\alpha_2} + \varphi}{\overline{\alpha_1} + \varphi}\right) = f\left(\frac{\alpha_2 + \alpha_2' + 2\varphi}{\alpha_1 + \alpha_1' + 2\varphi}\right)$$

or:

$$R = \sum_{i=0}^{n} k_i \cdot \left(\frac{\overline{\alpha_2} + \varphi}{\overline{\alpha_1} + \varphi}\right)^i$$

or:

$$R_L = \sum_{i=0}^{n} k_i \cdot \left(\frac{\alpha_2 + \varphi}{\alpha_1 + \varphi}\right)^i, R_R = \sum_{i=0}^{n} k_i \cdot \left(\frac{\alpha_2' + \varphi}{\alpha_1' + \varphi}\right)^i, R = \frac{R_L + R_R}{2}$$

or:

$$R = f\left(\frac{\tan(\alpha_2 + \varphi)}{\tan(\alpha_1 + \varphi)}, \frac{\tan(\alpha_2' + \varphi)}{\tan(\alpha_1' + \varphi)}\right)$$

or:

$$R_L = f\left(\frac{\tan(\alpha_2 + \varphi)}{\tan(\alpha_1 + \varphi)}\right), R_R = f\left(\frac{\tan(\alpha_2' + \varphi)}{\tan(\alpha_1' + \varphi)}\right), R = \frac{R_L + R_R}{2}$$

or:

$$R = f\left(\frac{\overline{t_2}}{\overline{t_1}}\right)$$

or:

$$R = \sum_{i=0}^{n} k_i \cdot \left(\frac{\overline{t_2}}{\overline{t_1}}\right)^i$$

wherein the coefficients $k_i$ are constant, n is a natural number such that $n \geq 1$, $\varphi$ is an angular offset such that $\varphi \in [-\pi, \pi]$, $\overline{\alpha_1}$ is the average value of angles $\alpha_1$ and $\alpha_1'$, $\overline{\alpha_2}$ is the average value of angles $\alpha_2$ and $\alpha_2'$, $$\left(\frac{\overline{\alpha_2} + \varphi}{\overline{\alpha_1} + \varphi}\right)^i$$

the i-th power of the ratio of the average angles with an angular offset $c\varphi$, $\overline{t_1}$ is the average value of the tangents of angles $\alpha_2$ and $$\alpha_2', \left(\frac{\overline{t_2}}{\overline{t_1}}\right)^i$$

is i-th power of the ratio of said average values of the tangents.

4) Method according to claim 3, wherein:

$$R = \frac{\tan(\alpha_2) + \tan(\alpha_2')}{\tan(\alpha_1) + \tan(\alpha_1')}$$

or:

$$R = \frac{R_L + R_R}{2} = \frac{\frac{\tan(\alpha_2)}{\tan(\alpha_1)} + \frac{\tan(\alpha_2')}{\tan(\alpha_1')}}{2} = \frac{\tan(\alpha_1)\tan(\alpha_2') + \tan(\alpha_1')\tan(\alpha_2)}{2\tan(\alpha_1)\tan(\alpha_1')}$$

5) Method according to any one of claims 1 to 4, wherein the parallel straight line (γ) is positioned in such a way that the line perpendicular to said parallel straight line (γ) and passing through $P_M$ intersects on said parallel straight line a point $P_H$ and on said base segment a point $P_B$ such that the segment $\overline{P_H P_B}$ is substantially equal to the segment $\overline{P_M P_H}$.

6) Method according to any claim 1-5, wherein in step D the numerical parameters of said mathematical transform depend at least by species and/or race and/or ethnicity and/or age of the subject and are obtained by comparison with a reference population evaluated according to a traditional method or a different measurement method of the prior art.

7) Method according to claim 6, wherein in step D the following substep is performed:

D1. correlating, by means of a first pre-defined mathematical transform, for example a linear transform, said numeric index R of step C with a visual and tactile scale of scores, such as for example the linear scoring or the body condition score of known use, in particular known in the traditional evaluation of body condition of production animals, affection animals, and man, and being obtained by comparison with a reference population evaluated by technical experts and/or by other means known in the art.

8) Method according to any one of claims 1 to 7, wherein after step C the following further step is performed:

E. correlating, using a second pre-defined mathematical transform, said numeric index R of step C, with the animal's weight, said mathematical transform depending at least on species and/or race and/or gender and/or age of the animal and being obtained by comparison with a reference population weighted by means of appropriate scales.

9) Method according to any one of claims 1 to 8, wherein after step C the following further step is performed:

F. correlating, by means of a further predefined mathematical transform, said numerical index R of step C with the degree of fertility of the subject under examination, resulting from the combination between the numerical index R and the state of estrus, detected by means of tools of the prior art.

10) Method according to any one of the preceding claims, wherein said profile is a profile of an anatomical region chosen in the group comprising the lumbar (L), abdominal (A), sacral (S), femoral (F), breast (P), gluteal (G), dorsal (D) region or the skull of the animal (107), in particular in their middle zone (M).

11) Method according to any one of the preceding claims, wherein said imaginary plane is a plane transverse to the spine of the animal.

12) Method according to any one of the preceding claims, wherein the detection system is a profilometer, such as triangulation scanners (e.g. laser lines with optical recording), time of flight and phase difference scanners or the comb gauges or flexometer sensors.

13) Method according to one of preceding claims, characterized in that the profile detected in step A is sent to a control unit (101), that carries out its compression and associates to it further data concerning said animal (107), and subsequently sends it to said at least one data processing unit (E), local or remote.

14) Method according to claim 13, characterized in that said further data are data detected by one or more sensors, in particular chosen in the set comprising: accelerometer, magnetometer, gyroscope, thermometer, GPS, Wi-Fi locator, RFID (radio frequency identification) reader, RTLS (real time locating system) locator, detection system of state of oestrus and personal details of the animal (107).

15) Method according to one of the claims 5 to 14, characterized in that said body condition score, prime body mass index or other scale of scores for the body condition, once the species and/or the ethnic group and/or the breed and/or sex are fixed, is obtainable from the numeric index R or synthetic fattening index, by means of a function of the type:

$$\sum_{i=0}^{n} k_i R^i$$

wherein n is an integer larger than 1, $R^i$ is the i-th power of R and parameters k are constants specific to the population to which said animal (107) belongs, determined for example by species and breed, and they are determined by comparison with a reference population evaluated visually or with others of prior art instruments, according to the traditional method.

16) Apparatus (D) for the determination of a numerical index indicative of energy reserves in the form of fat accumulated by an animal (107), comprising at least a contact or non-contact detection system (102, 103, 124, 125, 126, 128, 129, 130) for the detection of the a profile (109) of the animal (107), at least a control unit (101) and at least one data processing unit (E), local or remote, connected to said control unit (101), wherein said data processing unit (E), local or remote, includes a program so configured that, when executed, performs steps C and D of the method according to any one of claims 1 to 15.

17) Apparatus (D) according to the preceding claim, characterized in that said contact or non-contact detection system for detecting the profile (109) of the animal (107) can be alternately:

a) a camera (102) adapted to acquire images of one or more animals (107) with the profiles (109) highlighted by projection of coherent or not coherent light pattern or by beforehand application of paint or suitable adhesive or elastic bands on the body of the animal, said camera (102) being connected to said control unit (101), which integrates functions of digitization of the images and/or data compression and encryption and/or user interfacing, and/or data transmission;

b) an apparatus (PG) comprising a suitable number of needles (126) movable in a direction and at least one digitizing system (127) for digitizing the position of said needles, wherein said movable needles are configured to lean on the body of the animal (107), describing a profile (109) with a resolution proportional to their number, and wherein said digitizing system (127) is configured to convert the dislocation of said needles into an electrical signal processable by said data processing unit (E);

c) an apparatus (SG) comprising at least one band (131) sensitive to flexure, composed by a plurality of electronic strain gauges (130), and at least one signal digitizing system for digitizing the signal produced by said electronic strain gauges, wherein said band (131) sensitive to flexure is applied on the surface or under the animal skin (107), and by means of the electronic strain gauges (130) is configured to detect the expansion (132) or the compression (133) along the direction perpendicular to the spine the animal (107), in order to describe a profile (109) with a resolution proportional to the number of strain gauges integrated in said band (131), said electronic strain gauges being connected to said data processing unit (E).

18) Apparatus (D) according to claim 16 or 17, further comprising at least one position sensor (P) configured to detect the positioning of said apparatus (D) with respect to the position of said animal (107).

19) The apparatus (D) according to any of the claims from 16 to 18, wherein said apparatus (D) is portable and includes:
- an extension arm (105) adapted to be hold at a first end and that supports said control system (101), such as for example a smartphone, wherein said camera is integrated (102), on a second end;
- a laser arm (104) connectable to a first end to said extension arm (105) with which it forms for example a 135° angle, and comprising said laser generator (103) on a second end; and
- an actuator (106), disposed on said first end of said extension arm (105), configured to control said laser generator (103).

20) The apparatus (D) according to any one of claims from 16 to 19, characterized in that it comprises alternately a sensor of animal presence in a predetermined area, said sensor of the animal's presence sending its detection to said control unit (101) for the startup of step C of the method, or a reader of an identifying tag placed on said animal, said identifying tag reader being connected to said control unit (101).

21) Apparatus (D) according to any one of the preceding claims 16-20, characterized in that it comprises a system for detection of the estrus state of the animal according to prior art techniques, the combination of body condition score with the state of estrus providing a new indicator here defined as fertility index, determined according to the following formula:

$$F = E \cdot \frac{BCS_r}{BCS_i}$$

wherein E represents the state of estrus, in which E=0 in the absence of estrus and E=1 in the presence of estrus, $BCS_r$ the real value and $BCS_i$ the ideal value of the BCS of the animal, in which the fertility index F can take the following values and meanings:
- F=0, indicates the absence of oestrus, regardless of the body condition;
- F≅1 indicates oestrus condition and optimal body condition ($BCS_r \cong BCS_i$);
- F>1 indicates a state of oestrus in "overcondition";
- 0<F<1 indicates a state of oestrus in "undercondition".

The invention claimed is:

1. A method for determination of a numeric index indicative of energy reserves in the form of fat accumulated by an animal, dead or living of any species and race, including humans, the numeric index comprising a body condition score or a body mass index, the method comprising the following steps:
   A. digitally detecting, by optical detection of reference elements applied or projected on a body of the animal or by a profile detection system, with contact or without contact, at least a profile of an anatomical region of morphological interest, said at least a profile being defined as a shape of a curve that describes at least part of an outer perimeter of a section of said anatomical region, the curve lying on an imaginary plane intersecting said anatomical region;
   B. sending said at least a profile of step A to at least one data processing unit;
   C. calculating a numeric index R indicative of the energy reserves in the form of fat accumulated by the animal in said anatomical region, by at least a data processing unit on the basis of said at least a profile of step A; and
   D. correlating, in said at least one data processing unit, using a predefined mathematical transform, said numeric index R with one or more state features of said animal,
   wherein after step C the following further step is performed:
   F. correlating, using a further predefined mathematical transform, said numeric index R of step C with a degree of fertility of the animal under examination, resulting from a combination between the numeric index R and a detected state of estrus.

2. A method for determination of a numeric index indicative of energy reserves in the form of fat accumulated by an animal, dead or living of any species and race, including humans, the numeric index comprising a body condition score or a body mass index, the method comprising the following steps:
   A. digitally detecting, by optical detection of reference elements applied or projected on a body of the animal or by a profile detection system, with contact or without contact, at least a profile of an anatomical region of morphological interest, said at least a profile being defined as a shape of a curve that describes at least part of an outer perimeter of a section of said anatomical region, the curve lying on an imaginary plane intersecting said anatomical region;
   B. sending said at least a profile of step A to at least one data processing unit;
   C. calculating a numeric index R indicative of the energy reserves in the form of fat accumulated by the animal in said anatomical region, by at least a data processing unit on the basis of said at least a profile of step A; and
   D. correlating, in said at least one data processing unit, using a predefined mathematical transform, said numeric index R with one or more state features of said animal,
   wherein on the body of the animal a first side of said anatomical region with respect to a spine of the animal is present or a first side and a second side of said anatomical region with respect to the spine of the animal are present, and wherein said profile includes a point of relative maximum $P_M$ on the spine of the animal and a first development of the profile on said first side or a first and a second development of the profile respectively on said first and second side, wherein said step C includes the following sub-steps:
   C1. individuating coordinates of the relative maximum point $P_M$ of said profile;
   C2. determining a first straight line (β) tangent to said profile, said first straight line starting from the relative maximum point $P_M$ and touching said profile at a first point of tangency $P_1$ of said first side, or in addition to the first straight line of tangency determining also a second straight line of tangency (α) running from the point of relative maximum $P_M$ and touching said profile at a second point of tangency $P'_1$ on said second side;
   C3. in the case in which in step 2 only said first tangent point $P_1$ has been calculated, taking as the second development of said profile a specular projection of said first development with respect to a direction of the spine, and assuming as the second point of tangency P'$_1$ a point specular to said first point of tangency P$_1$ with respect to the direction of the spine;

C4. calculating a first broken line point P$_2$ and a second broken line point P'$_2$ as an intersection between said profile and a straight line ($\gamma$) parallel to a base segment which goes from P$_1$ to P'$_1$;

C5. calculating said numeric index R as:

$$R=f(\alpha_1,\alpha_2,\alpha'_1,\alpha'_2)$$

wherein $\alpha_2$ is an angle between segments $\overline{P_M P_2}$ and $\overline{P_2 P'_2}$, $\alpha_1$ is an angle between segments $\overline{P_2 P_1}$ and $\overline{P_1 P'_1}$, $\alpha'_2$ is an angle between segments $\overline{P_M P'_2}$ and $\overline{P'_2 P_2}$, $\alpha'_1$ is an angle between segments $\overline{P'_2 P'_1}$ and $\overline{P'_1 P_1}$, and wherein $\alpha_2=\alpha'_2$ and $\alpha_1=\alpha'_1$ in case of the assumption of step C3 has been made.

3. The method according to claim 2, wherein in step D numerical parameters of said mathematical transform depend by at least one of species, race, ethnicity, and age of the animal and are obtained by comparison with a reference population.

4. The method according to claim 3, wherein in step D the following substep is performed:

D1. correlating, using a first pre-defined mathematical transform comprising a linear transform, said numeric index R of step C with a visual and tactile scale of scores comprising a linear scoring or the body condition score of the animal, and being obtained by comparison with a reference population of the animal.

5. The method according to claim 4, wherein said body condition score, prime body mass index or scale of scores for the body condition, once at least one of the species, ethnic group, breed, and sex are fixed, is obtainable from the numeric index R or synthetic fattening index, using a function of the type:

$$\sum_{i=0}^{n} k_i R^i$$

wherein n is an integer larger than 1, $R^i$ is the i-th power of R and parameters $k_i$ are constants specific to a population to which said animal belongs, determined by species and breed, and determined by comparison with a reference population evaluated visually or with an instrument.

6. The method according to claim 2, wherein after step C the following further step is performed:

E. correlating, using a second pre-defined mathematical transform, said numeric index R of step C, with a weight of the animal, said mathematical transform depending on at least one of species, race, gender, age of the animal and being obtained by comparison with a reference population of the animal weighted by scales.

7. The method according to claim 2, wherein said profile is a profile of an anatomical region comprising a lumbar region, an abdominal region, a sacral region, a femoral region, a pectoral region, a gluteal region, a dorsal region, or a skull of the animal.

8. The method according to claim 2, wherein said imaginary plane is a plane transverse to a spine of the animal.

9. The method according to claim 2, wherein the profile detection system is a profilometer comprising triangulation scanners, time of flight and phase difference scanners, comb gauges, or flexometer sensors.

10. The method according to claim 2, wherein in step C5 first a synthetic index $R_L$ relevant to said first development and a synthetic index $R_R$ relevant to said second development are calculated as $$R_L=f(\alpha_1,\alpha_2), R_R=f(\alpha'_1,\alpha'_2)$$

and then:

$$R = \frac{R_L + R_R}{2}.$$

11. The method according to claim 2, wherein:

$$R=f(\overline{\alpha}_1,\overline{\alpha}_2)$$

or:

$$R = f\left(\frac{\alpha_2 + \varphi}{\alpha_1 + \varphi}, \frac{\alpha'_2 + \varphi}{\alpha'_1 + \varphi}\right)$$

or:

$$R = \left(\frac{R_L + R_R}{2}\right), \text{ wherein } R_L = f\left(\frac{\alpha_2 + \varphi}{\alpha_1 + \varphi}\right), R_R = f\left(\frac{\alpha'_2 + \varphi}{\alpha'_1 + \varphi}\right)$$

or:

$$R = f\left(\frac{\overline{\alpha}_2 + \varphi}{\overline{\alpha}_1 + \varphi}\right) = f\left(\frac{\alpha_2 + \alpha'_2 + 2\varphi}{\alpha_1 + \alpha'_1 + 2\varphi}\right)$$

or:

$$R = \sum_{i=0}^{n} k_i \cdot \left(\frac{\overline{\alpha}_2 + \varphi}{\overline{\alpha}_1 + \varphi}\right)^i$$

or:

$$R = \left(\frac{R_L + R_R}{2}\right), \text{ wherein } R_L = \sum_{i=0}^{n} k_i \cdot \left(\frac{\alpha_2 + \varphi}{\alpha_1 + \varphi}\right)^i, R_R = \sum_{i=0}^{n} k_i \cdot \left(\frac{\alpha'_2 + \varphi}{\alpha'_1 + \varphi}\right)^i$$

or:

$$R = f\left(\frac{\tan(\alpha_2 + \varphi)}{\tan(\alpha_1 + \varphi)}, \frac{\tan(\alpha'_2 + \varphi)}{\tan(\alpha'_1 + \varphi)}\right)$$

or:

$$R = \left(\frac{R_L + R_R}{2}\right), \text{ wherein } R_L = f\left(\frac{\tan(\alpha_2 + \varphi)}{\tan(\alpha_1 + \varphi)}\right), R_R = f\left(\frac{\tan(\alpha'_2 + \varphi)}{\tan(\alpha'_1 + \varphi)}\right)$$

or:

$$R = f\left(\frac{\bar{t}_2}{\bar{t}_1}\right)$$

or:

$$R = \sum_{i=0}^{n} k_i \cdot \left(\frac{\bar{t}_2}{\bar{t}_1}\right)^i$$

wherein the coefficients $k_i$ are constant, n is a natural number such that $n \geq 1$, $\varphi$ is an angular offset such that $\varphi \in [-\pi,\pi]$, $\bar{\alpha}_1$ is the average value of angles $\alpha_1$ and $\alpha'_1$, $\bar{\alpha}_2$ is the average value of angles $\alpha_2$ and $$\alpha'_2 \cdot \left(\frac{\bar{\alpha}_2 + \varphi}{\bar{\alpha}_1 + \varphi}\right)^i$$

the i-th power of the ratio of the average angles with an angular offset $\varphi$, $\bar{t}_1$ is the average value of the tangents of angles $\alpha_2$ and $$\alpha'_2 \cdot \left(\frac{\bar{t}_2}{\bar{t}_1}\right)^i$$

is i-th power of the ratio of said average values of the tangents.

12. The method according to claim 11, wherein:

$$R = \frac{\tan(\alpha_2) + \tan(\alpha'_2)}{\tan(\alpha_1) + \tan(\alpha'_1)}$$

or:

$$R = \frac{R_L + R_R}{2} = \frac{\frac{\tan(\alpha_2)}{\tan(\alpha_1)} + \frac{\tan(\alpha'_2)}{\tan(\alpha'_1)}}{2} = \frac{\tan(\alpha_1)\tan(\alpha'_2) + \tan(\alpha'_1)\tan(\alpha_2)}{2\tan(\alpha_1)\tan(\alpha'_1)}.$$

13. The method according to claim 2, wherein a parallel straight line ($\gamma$) is positioned in such a way that the line perpendicular to said parallel straight line ($\gamma$) and passing through $P_M$ intersects on said parallel straight line a point $P_H$ and on said base segment a point $P_B$ such that a segment $\overline{P_H P_B}$ is substantially equal to a segment $\overline{P_M P_H}$.

14. The method according to claim 2, wherein the profile detected in step A is sent to a control unit, that carries out a compression and associates to the profile further data concerning said animal, and subsequently sends the compression to said at least one data processing unit, local or remote.

15. The method according to claim 14, wherein said further data are data detected by one or more sensors comprising: an accelerometer, a magnetometer, a gyroscope, a thermometer, a GPS, a Wi-Fi locator, an RFID (radio frequency identification) reader, an RTLS (real time locating system) locator, or a detection system of state of estrus.

16. An apparatus for determination of a numeric index indicative of energy reserves in the form of fat accumulated by an animal, comprising at least a contact or non-contact detection system for detection of a profile of the animal, at least a control unit and at least one data processing unit, local or remote, connected to said control unit, wherein said data processing unit, local or remote, includes a program so configured that, when executed, performs steps C and D of the method according to any one of claims 3 to 5.

17. The apparatus for determination of a numeric index indicative of energy reserves in the form of fat accumulated by an animal according to claim 16, wherein said contact or non-contact detection system for detecting the profile of the animal is at least one of:
a) a camera adapted to acquire images of one or more animals with profiles highlighted by projection of coherent or not coherent light pattern or by beforehand application of paint or adhesive or elastic bands on the body of the animal, said camera being connected to said control unit, which integrates functions of at least one of: digitization of the images, data compression and encryption, user interfacing, and data transmission;
b) a prolifometer apparatus comprising a number of needles movable in a direction and at least one digitizing system for digitizing positions of said needles, wherein said movable needles are configured to lean on the body of the animal, describing a profile with a resolution proportional to the number of needles, and wherein said digitizing system is configured to convert a dislocation of said needles into an electrical signal processable by said data processing unit; and
c) a strain gauge apparatus comprising at least one band sensitive to flexure, composed by a plurality of electronic strain gauges, and at least one signal digitizing system for digitizing a signal produced by said electronic strain gauges, wherein said band sensitive to flexure is applied on a surface or under the animal skin, and by means of the electronic strain gauges is configured to detect an expansion or a compression along a direction perpendicular to a spine of the animal, in order to describe a profile with a resolution proportional to the number of strain gauges integrated in said band, said electronic strain gauges being connected to said data processing unit.

18. The apparatus (D) for determination of a numeric index indicative of energy reserves in the form of fat accumulated by an animal according to claim 16, further comprising at least one position sensor configured to detect the positioning of said apparatus with respect to the position of said animal.

19. An apparatus for determination of a numeric index indicative of energy reserves in the form of fat accumulated by an animal, comprising at least a contact or non-contact detection system for the detection of a profile of the animal, at least a control unit and at least one data processing unit, local or remote, connected to said control unit, wherein said data processing unit, local or remote, includes a program so configured that, when executed performs steps C and D of the method according to any one of claims 3 to 5, wherein said apparatus (D) is portable and includes:
an extension arm adapted to be held at a first end and that supports said control unit, wherein a camera is integrated, on a second end;
a laser arm connectable to a first end to said extension arm forming an angle, and comprising a laser generator on a second end; and
an actuator, disposed on said first end of said extension arm, configured to control said laser generator.

20. The apparatus (D) for determination of a numeric index indicative of energy reserves in the form of fat accumulated by an animal according to claim 16, further comprising: a sensor of animal presence in a predetermined area, said sensor of animal presence sending a detection signal to said control unit for step C of the method, or a reader of an identifying tag placed on said animal, said identifying tag reader being connected to said control unit.

21. An apparatus for determination of a numeric index indicative of energy reserves in the form of fat accumulated by an animal, comprising:
- at least a contact or non-contact detection system for the detection of a profile of the animal,
- at least a control unit and at least one data processing unit, local or remote, connected to said control unit, wherein said data processing unit, local or remote, includes a program so configured that, when executed performs a method comprising:
  - calculating a numeric index R indicative of the energy reserves in the form of fat accumulated by the animal in an anatomical region, by the at least a data processing unit on the basis of said profile; and
  - correlating, in said at least one data processing unit, using a predefined mathematical transform, said numeric index R with one or more state features of said animal; and
- a system for detection of an estrus state of the animal, a combination of a body condition score (BCS) with the state of estrus providing a new indicator here defined as fertility index F, determined according to the following formula:

$$F = E \cdot \frac{BCS_r}{BCS_i}$$

wherein E represents the state of estrus, in which E=0 in the absence of estrus and E=1 in the presence of estrus, $BCS_r$ is a real value of the BCS of the animal and $BCS_i$ is an ideal value of the BCS of the animal, in which the fertility index F has the following values and meanings:
- F=0, indicates the absence of estrus, regardless of the body condition score;
- F=1 indicates estrus condition and optimal body condition;
- F>1 indicates a state of estrus in overcondition; and
- 0<F<1 indicates a state of estrus in undercondition.

* * * * *